(12) United States Patent
Weisenburgh, II et al.

(10) Patent No.: US 11,484,191 B2
(45) Date of Patent: Nov. 1, 2022

(54) SYSTEM FOR PERFORMING A MINIMALLY INVASIVE SURGICAL PROCEDURE

(71) Applicant: Ethicon Endo-Surgery, Inc., Cincinnati, OH (US)

(72) Inventors: William B. Weisenburgh, II, Maineville, OH (US); Christopher J. Hess, Blue Ash, OH (US); Ragae M. Ghabrial, Pittsburgh, PA (US)

(73) Assignee: Cilag GmbH International, Zug (CH)

( * ) Notice: Subject to any disclaimer, the term of this patent is extended or adjusted under 35 U.S.C. 154(b) by 0 days.

(21) Appl. No.: 16/160,542

(22) Filed: Oct. 15, 2018

(65) Prior Publication Data

US 2019/0117054 A1 Apr. 25, 2019

Related U.S. Application Data

(62) Division of application No. 13/778,582, filed on Feb. 27, 2013, now Pat. No. 10,098,527.

(51) Int. Cl.
*A61B 1/05* (2006.01)
*A61B 1/00* (2006.01)
(Continued)

(52) U.S. Cl.
CPC .......... *A61B 1/053* (2013.01); *A61B 1/00158* (2013.01); *A61B 1/3132* (2013.01);
(Continued)

(58) Field of Classification Search
CPC .............. A61B 1/0014; A61B 1/00147; A61B 1/00158; A61B 1/3132; A61B 1/313;
(Continued)

(56) References Cited

U.S. PATENT DOCUMENTS 112,794 A 3/1871 Felton
645,576 A 3/1900 Tesla
(Continued)

FOREIGN PATENT DOCUMENTS

AU 666310 B2 2/1996
DE 19713797 A1 10/1997
(Continued)

OTHER PUBLICATIONS

Michael S. Kavic, M.D., "Natural Orifice Translumenal Endoscopic Surgery: "NOTES"", JSLS, vol. 10, pp. 133-134 (2006).
(Continued)

*Primary Examiner* — John P Leubecker
*Assistant Examiner* — Jae Woo

(57) ABSTRACT

A surgical system for performing a surgical procedure includes an ex-vivo positioning mechanism and an in-vivo instrument magnetically attracted to the ex-vivo positioning mechanism. The in-vivo instrument can be positioned within a patient by moving the ex-vivo positioning mechanism. In addition, the surgical system includes a percutaneous member introducible into the patient independent from the ex-vivo positioning mechanism, the percutaneous member comprising a connector at a distal end thereof, wherein the connector is selectively couplable to the in-vivo instrument within the patient.

16 Claims, 8 Drawing Sheets

(51) Int. Cl.
*A61B 1/313* (2006.01)
*A61B 17/00* (2006.01)
*A61B 90/00* (2016.01)
*A61B 90/30* (2016.01)

(52) U.S. Cl.
CPC ............ *A61B 2017/00283* (2013.01); *A61B 2017/00473* (2013.01); *A61B 2017/00876* (2013.01); *A61B 2090/309* (2016.02); *A61B 2090/3612* (2016.02); *A61B 2090/371* (2016.02)

(58) Field of Classification Search
CPC ...... A61B 2090/309; A61B 2090/3612; A61B 2090/371
See application file for complete search history.

(56) References Cited

U.S. PATENT DOCUMENTS

| | | | |
|---|---|---|---|
| 649,621 A | 5/1900 | Tesla |
| 787,412 A | 4/1905 | Tesla |
| 1,039,354 A | 9/1912 | Bonadio |
| 1,127,948 A | 2/1915 | Wappler |
| 1,330,147 A | 2/1920 | Stitzer |
| 1,330,205 A | 2/1920 | McKeehan |
| 1,335,331 A | 3/1920 | Gunderson |
| 1,440,116 A | 12/1922 | Telfer |
| 1,482,653 A | 2/1924 | Lilly |
| 1,581,706 A | 4/1926 | White |
| 1,581,707 A | 4/1926 | White |
| 1,581,708 A | 4/1926 | White |
| 1,581,709 A | 4/1926 | White |
| 1,581,710 A | 4/1926 | White |
| 1,625,602 A | 4/1927 | Gould |
| 1,892,018 A | 12/1932 | Stanton |
| 1,916,722 A | 7/1933 | Ende |
| 2,028,635 A | 1/1936 | Wappler |
| 2,031,682 A | 2/1936 | Wappler |
| 2,113,246 A | 4/1938 | Wappler |
| 2,137,710 A | 11/1938 | Anderson |
| 2,155,365 A | 4/1939 | Rankin |
| 2,191,858 A | 2/1940 | Moore |
| 2,196,620 A | 4/1940 | Attarian |
| 2,303,961 A | 12/1942 | Sprague |
| 2,330,120 A | 9/1943 | Hagelstein |
| 2,388,137 A | 10/1945 | Graumlich |
| 2,409,379 A | 10/1946 | Mosaly |
| 2,451,077 A | 10/1948 | Emsig |
| 2,493,108 A | 1/1950 | Casey |
| 2,504,152 A | 4/1950 | Riker |
| 2,514,698 A | 7/1950 | Herrero |
| 2,514,951 A | 7/1950 | Herndon |
| 2,644,210 A | 7/1953 | McNamee |
| 2,938,382 A | 5/1960 | De Graaf |
| 2,952,206 A | 9/1960 | Becksted |
| 3,044,461 A | 7/1962 | Murdock |
| 3,069,195 A | 12/1962 | Buck |
| 3,070,088 A | 12/1962 | Brahos |
| 3,110,956 A | 11/1963 | Fischer, Jr. |
| 3,170,471 A | 2/1965 | Schnitzer |
| 3,435,824 A | 4/1969 | Gamponia |
| 3,470,876 A | 10/1969 | Barchilon |
| 3,481,325 A | 12/1969 | Glassman |
| 3,543,760 A | 12/1970 | Bolduc |
| 3,595,239 A | 7/1971 | Petersen |
| 3,669,487 A | 6/1972 | Roberts et al. |
| 3,746,881 A | 7/1973 | Fitch et al. |
| 3,799,672 A | 3/1974 | Vurek |
| 3,854,473 A | 12/1974 | Matsuo |
| 3,854,743 A | 12/1974 | Hansen |
| 3,929,123 A | 12/1975 | Jamshidi |
| 3,946,740 A | 3/1976 | Bassett |
| 3,948,251 A | 4/1976 | Hosono |
| 3,961,632 A | 6/1976 | Moossun |
| 3,965,890 A | 6/1976 | Gauthier |
| 3,994,301 A | 11/1976 | Agris |
| 4,011,872 A | 3/1977 | Komiya |
| 4,012,812 A | 3/1977 | Black |
| 4,043,342 A | 8/1977 | Morrison, Jr. |
| 4,071,028 A | 1/1978 | Perkins |
| 4,085,743 A | 4/1978 | Yoon |
| 4,164,225 A | 8/1979 | Johnson et al. |
| 4,170,997 A | 10/1979 | Pinnow et al. |
| 4,174,715 A | 11/1979 | Hasson |
| 4,178,920 A | 12/1979 | Cawood, Jr. et al. |
| 4,207,873 A | 6/1980 | Kruy |
| 4,235,238 A | 11/1980 | Ogiu et al. |
| 4,258,716 A | 3/1981 | Sutherland |
| 4,269,174 A | 5/1981 | Adair |
| 4,278,077 A | 7/1981 | Mizumoto |
| 4,281,646 A | 8/1981 | Kinoshita |
| 4,285,344 A | 8/1981 | Marshall |
| 4,311,143 A | 1/1982 | Komiya |
| 4,329,980 A | 5/1982 | Terada |
| 4,393,872 A | 7/1983 | Reznik et al. |
| 4,394,791 A | 7/1983 | Groth |
| 4,396,021 A | 8/1983 | Baumgartner |
| 4,396,139 A | 8/1983 | Hall et al. |
| 4,406,656 A | 9/1983 | Hattler et al. |
| 4,452,246 A | 6/1984 | Bader et al. |
| 4,461,281 A | 7/1984 | Carson |
| 4,491,132 A | 1/1985 | Aikins |
| 4,491,135 A | 1/1985 | Klein |
| 4,492,232 A | 1/1985 | Green |
| 4,527,331 A | 7/1985 | Lasner et al. |
| 4,527,564 A | 7/1985 | Eguchi et al. |
| 4,538,594 A | 9/1985 | Boebel et al. |
| D281,104 S | 10/1985 | Davison |
| 4,569,347 A | 2/1986 | Frisbie |
| 4,580,551 A | 4/1986 | Siegmund et al. |
| 4,646,722 A | 3/1987 | Silverstein et al. |
| 4,649,904 A | 3/1987 | Krauter et al. |
| 4,653,476 A | 3/1987 | Bonnet |
| 4,655,219 A | 4/1987 | Petruzzi |
| 4,657,016 A | 4/1987 | Garito et al. |
| 4,657,018 A | 4/1987 | Hakky |
| 4,669,470 A | 6/1987 | Brandfield |
| 4,671,477 A | 6/1987 | Cullen |
| 4,677,982 A | 7/1987 | Llinas et al. |
| 4,685,447 A | 8/1987 | Iversen et al. |
| 4,711,239 A | 12/1987 | Sorochenko et al. |
| 4,711,240 A | 12/1987 | Goldwasser et al. |
| 4,712,545 A | 12/1987 | Honkanen |
| 4,721,116 A | 1/1988 | Schintgen et al. |
| 4,727,600 A | 2/1988 | Avakian |
| 4,733,662 A | 3/1988 | DeSatnick et al. |
| D295,894 S | 5/1988 | Sharkany et al. |
| 4,742,817 A | 5/1988 | Kawashima et al. |
| 4,753,223 A | 6/1988 | Bremer |
| 4,763,669 A | 8/1988 | Jaeger |
| 4,770,188 A | 9/1988 | Chikama |
| 4,790,624 A | 12/1988 | Van Hoye et al. |
| 4,791,707 A | 12/1988 | Tucker |
| 4,796,627 A | 1/1989 | Tucker |
| 4,807,593 A | 2/1989 | Ito |
| 4,815,450 A | 3/1989 | Patel |
| 4,819,620 A | 4/1989 | Okutsu |
| 4,823,794 A | 4/1989 | Pierce |
| 4,829,999 A | 5/1989 | Auth |
| 4,836,188 A | 6/1989 | Berry |
| 4,846,573 A | 7/1989 | Taylor et al. |
| 4,867,140 A | 9/1989 | Hovis et al. |
| 4,869,238 A | 9/1989 | Opie et al. |
| 4,869,459 A | 9/1989 | Bourne |
| 4,873,979 A | 10/1989 | Hanna |
| 4,880,015 A | 11/1989 | Nierman |
| 4,904,048 A | 2/1990 | Sogawa et al. |
| 4,911,148 A | 3/1990 | Sosnowski et al. |
| 4,926,860 A | 5/1990 | Stice et al. |
| 4,934,364 A | 6/1990 | Green |
| 4,938,214 A | 7/1990 | Specht et al. |
| 4,950,273 A | 8/1990 | Briggs |
| 4,950,285 A | 8/1990 | Wilk |

(56) References Cited

U.S. PATENT DOCUMENTS

| | | |
|---|---|---|
| 4,953,539 A | 9/1990 | Nakamura et al. |
| 4,960,133 A | 10/1990 | Hewson |
| 4,977,887 A | 12/1990 | Gouda |
| 4,979,496 A | 12/1990 | Komi |
| 4,979,950 A | 12/1990 | Transue et al. |
| 4,984,581 A | 1/1991 | Stice |
| 4,990,152 A | 2/1991 | Yoon |
| 4,991,565 A | 2/1991 | Takahashi et al. |
| 4,994,079 A | 2/1991 | Genese et al. |
| 5,007,917 A | 4/1991 | Evans |
| 5,010,876 A | 4/1991 | Henley et al. |
| 5,015,249 A | 5/1991 | Nakao et al. |
| 5,020,514 A | 6/1991 | Heckele |
| 5,020,535 A | 6/1991 | Parker et al. |
| 5,025,778 A | 6/1991 | Silverstein et al. |
| 5,026,379 A | 6/1991 | Yoon |
| 5,033,169 A | 7/1991 | Bindon |
| 5,037,433 A | 8/1991 | Wilk et al. |
| 5,041,129 A | 8/1991 | Hayhurst et al. |
| 5,046,513 A | 9/1991 | Gatturna et al. |
| 5,049,153 A | 9/1991 | Nakao et al. |
| 5,050,585 A | 9/1991 | Takahashi |
| 5,052,372 A | 10/1991 | Shapiro |
| 5,065,516 A | 11/1991 | Dulebohn |
| 5,066,295 A | 11/1991 | Kozak et al. |
| 5,098,378 A | 3/1992 | Piontek et al. |
| 5,099,827 A | 3/1992 | Melzer et al. |
| 5,108,421 A | 4/1992 | Fowler |
| 5,123,913 A | 6/1992 | Wilk et al. |
| 5,123,914 A | 6/1992 | Cope |
| 5,133,727 A | 7/1992 | Bales et al. |
| 5,147,374 A | 9/1992 | Fernandez |
| 5,156,151 A | 10/1992 | Imran |
| 5,156,609 A | 10/1992 | Nakao et al. |
| 5,174,300 A | 12/1992 | Bales et al. |
| 5,176,126 A | 1/1993 | Chikama |
| 5,180,373 A | 1/1993 | Green et al. |
| 5,190,050 A | 3/1993 | Nitzsche |
| 5,190,555 A | 3/1993 | Wetter et al. |
| 5,192,284 A | 3/1993 | Pleatman |
| 5,192,300 A | 3/1993 | Fowler |
| 5,197,963 A | 3/1993 | Parins |
| 5,201,752 A | 4/1993 | Brown et al. |
| 5,201,908 A | 4/1993 | Jones |
| 5,203,785 A | 4/1993 | Slater |
| 5,203,787 A | 4/1993 | Noblitt et al. |
| 5,209,747 A | 5/1993 | Knoepfler |
| 5,217,003 A | 6/1993 | Wilk |
| 5,217,453 A | 6/1993 | Wilk |
| 5,219,357 A | 6/1993 | Honkanen et al. |
| 5,219,358 A | 6/1993 | Bendel et al. |
| 5,222,362 A | 6/1993 | Maus et al. |
| 5,222,961 A | 6/1993 | Nakao et al. |
| 5,222,965 A | 6/1993 | Haughton |
| 5,224,946 A | 7/1993 | Hayhurst et al. |
| 5,234,437 A | 8/1993 | Sepetka |
| 5,234,453 A | 8/1993 | Smith et al. |
| 5,235,964 A | 8/1993 | Abenalm |
| 5,242,456 A | 9/1993 | Nash et al. |
| 5,245,460 A | 9/1993 | Allen et al. |
| 5,246,424 A | 9/1993 | Wilk |
| 5,254,130 A | 10/1993 | Poncet et al. |
| 5,256,149 A | 10/1993 | Banik et al. |
| 5,257,999 A | 11/1993 | Slanetz, Jr. |
| 5,259,366 A | 11/1993 | Reydel et al. |
| 5,263,958 A | 11/1993 | deGuillebon et al. |
| 5,273,524 A | 12/1993 | Fox et al. |
| 5,275,607 A | 1/1994 | Lo et al. |
| 5,275,614 A | 1/1994 | Haber et al. |
| 5,275,616 A | 1/1994 | Fowler |
| 5,284,128 A | 2/1994 | Hart |
| 5,284,162 A | 2/1994 | Wilk |
| 5,287,845 A | 2/1994 | Faul et al. |
| 5,287,852 A | 2/1994 | Arkinstall |
| 5,290,299 A | 3/1994 | Fain et al. |
| 5,290,302 A | 3/1994 | Pericic |
| 5,295,977 A | 3/1994 | Cohen et al. |
| 5,297,536 A | 3/1994 | Wilk |
| 5,297,687 A | 3/1994 | Freed |
| 5,301,061 A | 4/1994 | Nakada et al. |
| 5,308,327 A | 5/1994 | Heaven et al. |
| 5,312,023 A | 5/1994 | Green et al. |
| 5,312,333 A | 5/1994 | Churinetz et al. |
| 5,312,351 A | 5/1994 | Gerrone |
| 5,312,416 A | 5/1994 | Spaeth et al. |
| 5,312,423 A | 5/1994 | Rosenbluth et al. |
| 5,318,589 A | 6/1994 | Lichtman |
| 5,320,636 A | 6/1994 | Slater |
| 5,324,261 A | 6/1994 | Amundson et al. |
| 5,325,845 A | 7/1994 | Adair |
| 5,330,471 A | 7/1994 | Eggers |
| 5,330,486 A | 7/1994 | Wilk |
| 5,330,488 A | 7/1994 | Rath |
| 5,330,496 A | 7/1994 | Alferness |
| 5,330,502 A | 7/1994 | Hassler et al. |
| 5,331,971 A | 7/1994 | Bales et al. |
| 5,334,168 A | 8/1994 | Hemmer |
| 5,334,198 A | 8/1994 | Hart et al. |
| 5,336,192 A | 8/1994 | Palestrant |
| 5,336,222 A | 8/1994 | Durgin, Jr. et al. |
| 5,339,805 A | 8/1994 | Parker |
| 5,341,815 A | 8/1994 | Cofone et al. |
| 5,342,396 A | 8/1994 | Cook |
| 5,344,428 A | 9/1994 | Griffiths |
| 5,345,927 A | 9/1994 | Bonutti |
| 5,348,259 A | 9/1994 | Blanco et al. |
| 5,350,391 A | 9/1994 | Iacovelli |
| 5,352,184 A | 10/1994 | Goldberg et al. |
| 5,352,222 A | 10/1994 | Rydell |
| 5,354,302 A | 10/1994 | Ko |
| 5,354,311 A | 10/1994 | Kambin et al. |
| 5,356,381 A | 10/1994 | Ensminger et al. |
| 5,356,408 A | 10/1994 | Rydell |
| 5,360,428 A | 11/1994 | Hutchinson, Jr. |
| 5,364,408 A | 11/1994 | Gordon |
| 5,364,410 A | 11/1994 | Failla et al. |
| 5,366,466 A | 11/1994 | Christian et al. |
| 5,366,467 A | 11/1994 | Lynch et al. |
| 5,368,605 A | 11/1994 | Miller, Jr. |
| 5,368,606 A | 11/1994 | Marlow et al. |
| 5,370,647 A | 12/1994 | Graber et al. |
| 5,370,679 A | 12/1994 | Atlee, III |
| 5,374,273 A | 12/1994 | Nakao et al. |
| 5,374,275 A | 12/1994 | Bradley et al. |
| 5,374,277 A | 12/1994 | Hassler |
| 5,374,953 A | 12/1994 | Sasaki et al. |
| 5,376,077 A | 12/1994 | Gomringer |
| 5,377,695 A | 1/1995 | An Haack |
| 5,378,234 A | 1/1995 | Hammerslag et al. |
| 5,383,877 A | 1/1995 | Clarke |
| 5,383,888 A | 1/1995 | Zvenyatsky et al. |
| 5,386,817 A | 2/1995 | Jones |
| 5,387,259 A | 2/1995 | Davidson |
| 5,391,174 A | 2/1995 | Weston |
| 5,392,789 A | 2/1995 | Slater et al. |
| 5,395,367 A | 3/1995 | Wilk |
| 5,395,381 A | 3/1995 | Green et al. |
| 5,395,386 A | 3/1995 | Slater |
| 5,397,332 A | 3/1995 | Kammerer et al. |
| 5,401,248 A | 3/1995 | Bencini |
| 5,403,311 A | 4/1995 | Abele et al. |
| 5,403,326 A | 4/1995 | Harrison et al. |
| 5,403,328 A | 4/1995 | Shallman |
| 5,403,342 A | 4/1995 | Tovey et al. |
| 5,403,348 A | 4/1995 | Bonutti |
| 5,405,073 A | 4/1995 | Porter |
| 5,405,359 A | 4/1995 | Pierce |
| 5,409,478 A | 4/1995 | Gerry et al. |
| 5,417,699 A | 5/1995 | Klein et al. |
| 5,423,821 A | 6/1995 | Pasque |
| 5,431,635 A | 7/1995 | Yoon |
| 5,433,721 A | 7/1995 | Hooven et al. |
| 5,433,735 A | 7/1995 | Zanakis et al. |
| 5,439,471 A | 8/1995 | Kerr |

(56) References Cited

U.S. PATENT DOCUMENTS

| | | |
|---|---|---|
| 5,439,478 A | 8/1995 | Palmer |
| 5,441,059 A | 8/1995 | Dannan |
| 5,441,494 A | 8/1995 | Ortiz |
| 5,441,498 A | 8/1995 | Perkins |
| 5,441,499 A | 8/1995 | Fritzsch |
| 5,443,463 A | 8/1995 | Stern et al. |
| 5,445,638 A | 8/1995 | Rydell et al. |
| 5,445,648 A | 8/1995 | Cook |
| 5,449,021 A | 9/1995 | Chikama |
| 5,454,827 A | 10/1995 | Aust et al. |
| 5,456,667 A | 10/1995 | Ham et al. |
| 5,456,684 A | 10/1995 | Schmidt et al. |
| 5,458,131 A | 10/1995 | Wilk |
| 5,458,583 A | 10/1995 | McNeely et al. |
| 5,460,168 A | 10/1995 | Masubuchi et al. |
| 5,460,629 A | 10/1995 | Shlain et al. |
| 5,462,561 A | 10/1995 | Voda |
| 5,465,731 A | 11/1995 | Bell et al. |
| 5,467,763 A | 11/1995 | McMahon et al. |
| 5,468,250 A | 11/1995 | Paraschac et al. |
| 5,470,308 A | 11/1995 | Edwards et al. |
| 5,470,320 A | 11/1995 | Tiefenbrun et al. |
| 5,472,441 A | 12/1995 | Edwards et al. |
| 5,478,347 A | 12/1995 | Aranyi |
| 5,478,352 A | 12/1995 | Fowler |
| 5,480,404 A | 1/1996 | Kammerer et al. |
| 5,482,029 A | 1/1996 | Sekiguchi et al. |
| 5,482,054 A | 1/1996 | Slater et al. |
| 5,484,451 A | 1/1996 | Akopov et al. |
| 5,489,256 A | 2/1996 | Adair |
| 5,496,347 A | 3/1996 | Hashiguchi et al. |
| 5,499,990 A | 3/1996 | Schulken et al. |
| 5,499,992 A | 3/1996 | Meade et al. |
| 5,499,997 A | 3/1996 | Sharpe et al. |
| 5,500,012 A | 3/1996 | Brucker et al. |
| 5,501,692 A | 3/1996 | Riza |
| 5,503,616 A | 4/1996 | Jones |
| 5,505,686 A | 4/1996 | Willis et al. |
| 5,507,755 A | 4/1996 | Gresl et al. |
| 5,511,564 A | 4/1996 | Wilk |
| 5,514,157 A | 5/1996 | Nicholas et al. |
| 5,518,501 A | 5/1996 | Oneda et al. |
| 5,522,829 A | 6/1996 | Michalos |
| 5,522,830 A | 6/1996 | Aranyi |
| 5,524,633 A | 6/1996 | Heaven et al. |
| 5,527,321 A | 6/1996 | Hinchliffe |
| 5,533,418 A | 7/1996 | Wu et al. |
| 5,536,234 A | 7/1996 | Newman |
| 5,536,248 A | 7/1996 | Weaver et al. |
| 5,538,509 A | 7/1996 | Dunlap et al. |
| 5,540,648 A | 7/1996 | Yoon |
| 5,549,637 A | 8/1996 | Crainich |
| 5,554,151 A | 9/1996 | Hinchliffe |
| 5,555,883 A | 9/1996 | Avitall |
| 5,558,133 A | 9/1996 | Bortoli et al. |
| 5,562,693 A | 10/1996 | Devlin et al. |
| 5,569,205 A | 10/1996 | Hart et al. |
| 5,569,243 A | 10/1996 | Kortenbach et al. |
| 5,569,298 A | 10/1996 | Schnell |
| 5,571,090 A | 11/1996 | Sherts |
| 5,573,540 A | 11/1996 | Yoon |
| 5,578,030 A | 11/1996 | Levin |
| 5,582,611 A | 12/1996 | Tsuruta et al. |
| 5,582,617 A | 12/1996 | Klieman et al. |
| 5,584,845 A | 12/1996 | Hart |
| 5,590,660 A | 1/1997 | MacAulay et al. |
| 5,591,179 A | 1/1997 | Edelstein |
| 5,591,205 A | 1/1997 | Fowler |
| 5,593,420 A | 1/1997 | Eubanks, Jr. et al. |
| 5,595,562 A | 1/1997 | Grier |
| 5,597,378 A | 1/1997 | Jervis |
| 5,601,573 A | 2/1997 | Fogelberg et al. |
| 5,601,574 A | 2/1997 | Stefanchik et al. |
| 5,601,588 A | 2/1997 | Tonomura et al. |
| 5,601,602 A | 2/1997 | Fowler |
| 5,604,531 A | 2/1997 | Iddan et al. |
| 5,607,386 A | 3/1997 | Flam |
| 5,607,389 A | 3/1997 | Edwards et al. |
| 5,607,406 A | 3/1997 | Hernandez et al. |
| 5,607,450 A | 3/1997 | Zvenyatsky et al. |
| 5,609,601 A | 3/1997 | Kolesa et al. |
| 5,611,803 A | 3/1997 | Heaven et al. |
| 5,613,975 A | 3/1997 | Christy |
| 5,613,977 A | 3/1997 | Weber et al. |
| 5,614,943 A | 3/1997 | Nakamura et al. |
| 5,616,117 A | 4/1997 | Dinkier et al. |
| 5,618,303 A | 4/1997 | Marlow et al. |
| 5,620,415 A | 4/1997 | Lucey et al. |
| 5,624,399 A | 4/1997 | Ackerman |
| 5,624,431 A | 4/1997 | Gerry et al. |
| 5,626,578 A | 5/1997 | Tihon |
| 5,626,587 A | 5/1997 | Bishop et al. |
| 5,628,732 A | 5/1997 | Antoon, Jr. et al. |
| 5,630,782 A | 5/1997 | Adair |
| 5,630,795 A | 5/1997 | Kuramoto et al. |
| 5,643,283 A | 7/1997 | Younker |
| 5,643,292 A | 7/1997 | Hart |
| 5,643,294 A | 7/1997 | Tovey et al. |
| 5,644,798 A | 7/1997 | Shah |
| 5,645,083 A | 7/1997 | Essig et al. |
| 5,645,519 A | 7/1997 | Lee et al. |
| 5,645,565 A | 7/1997 | Rudd et al. |
| 5,649,372 A | 7/1997 | Souza |
| 5,653,677 A | 8/1997 | Okada et al. |
| 5,653,690 A | 8/1997 | Booth et al. |
| 5,653,722 A | 8/1997 | Kieturakis |
| 5,657,755 A | 8/1997 | Desai |
| 5,662,621 A | 9/1997 | Lafontaine |
| 5,662,663 A | 9/1997 | Shallman |
| 5,665,096 A | 9/1997 | Yoon |
| 5,665,100 A | 9/1997 | Yoon |
| 5,667,527 A | 9/1997 | Cook |
| 5,669,875 A | 9/1997 | van Eerdenburg |
| 5,681,276 A | 10/1997 | Lundquist |
| 5,681,279 A | 10/1997 | Roper et al. |
| 5,681,324 A | 10/1997 | Kammerer et al. |
| 5,681,330 A | 10/1997 | Hughett et al. |
| 5,685,820 A | 11/1997 | Riek et al. |
| 5,688,269 A | 11/1997 | Newton et al. |
| 5,690,606 A | 11/1997 | Slotman |
| 5,690,656 A | 11/1997 | Cope et al. |
| 5,690,660 A | 11/1997 | Kauker et al. |
| 5,695,448 A | 12/1997 | Kimura et al. |
| 5,695,505 A | 12/1997 | Yoon |
| 5,695,511 A | 12/1997 | Cano et al. |
| 5,700,275 A | 12/1997 | Bell et al. |
| 5,702,438 A | 12/1997 | Avitall |
| 5,704,892 A | 1/1998 | Adair |
| 5,709,708 A | 1/1998 | Thal |
| 5,711,921 A | 1/1998 | Langford |
| 5,716,326 A | 2/1998 | Dannan |
| 5,716,375 A | 2/1998 | Fowler |
| 5,725,542 A | 3/1998 | Yoon |
| 5,728,094 A | 3/1998 | Edwards |
| 5,730,740 A | 3/1998 | Wales et al. |
| 5,735,849 A | 4/1998 | Baden et al. |
| 5,741,234 A | 4/1998 | Aboul-Hosn |
| 5,741,278 A | 4/1998 | Stevens |
| 5,741,285 A | 4/1998 | McBrayer et al. |
| 5,741,429 A | 4/1998 | Donadio, III et al. |
| 5,743,456 A | 4/1998 | Jones et al. |
| 5,746,759 A | 5/1998 | Meade et al. |
| 5,749,826 A | 5/1998 | Faulkner |
| 5,749,881 A | 5/1998 | Sackler et al. |
| 5,749,889 A | 5/1998 | Bacich et al. |
| 5,752,951 A | 5/1998 | Yanik |
| 5,755,731 A | 5/1998 | Grinberg |
| 5,759,150 A | 6/1998 | Konou et al. |
| 5,759,151 A | 6/1998 | Sturges |
| 5,762,604 A | 6/1998 | Kieturakis |
| 5,766,167 A | 6/1998 | Eggers et al. |
| 5,766,170 A | 6/1998 | Eggers |
| 5,766,205 A | 6/1998 | Zvenyatsky et al. |
| 5,769,849 A | 6/1998 | Eggers |

(56) References Cited

U.S. PATENT DOCUMENTS

| | | |
|---|---|---|
| 5,776,188 A | 7/1998 | Shepherd et al. |
| 5,779,701 A | 7/1998 | McBrayer et al. |
| 5,779,716 A | 7/1998 | Cano et al. |
| 5,779,720 A | 7/1998 | Walder-Utz et al. |
| 5,779,727 A | 7/1998 | Orejola |
| 5,782,748 A | 7/1998 | Palmer et al. |
| 5,782,859 A | 7/1998 | Nicholas et al. |
| 5,782,861 A | 7/1998 | Cragg et al. |
| 5,782,866 A | 7/1998 | Wenstrom, Jr. |
| 5,791,022 A | 8/1998 | Bohman |
| 5,792,113 A | 8/1998 | Kramer et al. |
| 5,792,153 A | 8/1998 | Swain et al. |
| 5,792,165 A | 8/1998 | Klieman et al. |
| 5,797,835 A | 8/1998 | Green |
| 5,797,928 A | 8/1998 | Kogasaka |
| 5,797,939 A | 8/1998 | Yoon |
| 5,797,941 A | 8/1998 | Schulze et al. |
| 5,797,959 A | 8/1998 | Castro et al. |
| 5,797,960 A | 8/1998 | Stevens et al. |
| 5,800,449 A | 9/1998 | Wales |
| 5,800,451 A | 9/1998 | Buess et al. |
| 5,803,903 A | 9/1998 | Athas et al. |
| 5,807,395 A | 9/1998 | Mulier et al. |
| 5,808,665 A | 9/1998 | Green |
| 5,810,805 A | 9/1998 | Sutcu et al. |
| 5,810,806 A | 9/1998 | Ritchart et al. |
| 5,810,849 A | 9/1998 | Kontos |
| 5,810,865 A | 9/1998 | Koscher et al. |
| 5,810,876 A | 9/1998 | Kelleher |
| 5,810,877 A | 9/1998 | Roth et al. |
| 5,813,976 A | 9/1998 | Filipi et al. |
| 5,814,026 A | 9/1998 | Yoon |
| 5,814,058 A | 9/1998 | Carlson et al. |
| 5,817,061 A | 10/1998 | Goodwin et al. |
| 5,817,107 A | 10/1998 | Schaller |
| 5,817,108 A | 10/1998 | Poncet |
| 5,817,119 A | 10/1998 | Klieman et al. |
| 5,818,527 A | 10/1998 | Yamaguchi et al. |
| 5,819,736 A | 10/1998 | Avny et al. |
| 5,823,947 A | 10/1998 | Yoon et al. |
| 5,824,071 A | 10/1998 | Nelson et al. |
| 5,827,190 A | 10/1998 | Palcic et al. |
| 5,827,276 A | 10/1998 | LeVeen et al. |
| 5,827,281 A | 10/1998 | Levin |
| 5,827,299 A | 10/1998 | Thomason et al. |
| 5,827,323 A | 10/1998 | Klieman et al. |
| 5,830,221 A | 11/1998 | Stein et al. |
| 5,830,231 A | 11/1998 | Geiges, Jr. |
| 5,833,603 A | 11/1998 | Kovacs et al. |
| 5,833,700 A | 11/1998 | Fogelberg et al. |
| 5,833,703 A | 11/1998 | Manushakian |
| 5,833,715 A | 11/1998 | Vachon et al. |
| 5,836,960 A | 11/1998 | Kolesa et al. |
| 5,843,017 A | 12/1998 | Yoon |
| 5,843,097 A | 12/1998 | Mayenberger et al. |
| 5,843,121 A | 12/1998 | Yoon |
| 5,843,156 A | 12/1998 | Slepian et al. |
| 5,846,238 A | 12/1998 | Jackson et al. |
| 5,848,986 A | 12/1998 | Lundquist et al. |
| 5,849,022 A | 12/1998 | Sakashita et al. |
| 5,853,374 A | 12/1998 | Hart et al. |
| 5,855,569 A | 1/1999 | Komi |
| 5,855,585 A | 1/1999 | Kontos |
| 5,860,913 A | 1/1999 | Yamaya et al. |
| 5,860,995 A | 1/1999 | Berkelaar |
| 5,868,762 A | 2/1999 | Cragg et al. |
| 5,873,849 A | 2/1999 | Bernard |
| 5,876,411 A | 3/1999 | Kontos |
| 5,882,331 A | 3/1999 | Sasaki |
| 5,882,344 A | 3/1999 | Stouder, Jr. |
| 5,885,280 A | 3/1999 | Nettekoven et al. |
| 5,893,846 A | 4/1999 | Bales et al. |
| 5,893,874 A | 4/1999 | Bourque et al. |
| 5,893,875 A | 4/1999 | O'Connor et al. |
| 5,897,487 A | 4/1999 | Ouchi |
| 5,899,919 A | 5/1999 | Eubanks, Jr. et al. |
| 5,902,238 A | 5/1999 | Golden et al. |
| 5,902,254 A | 5/1999 | Magram |
| 5,904,702 A | 5/1999 | Ek et al. |
| 5,906,625 A | 5/1999 | Bito et al. |
| 5,908,420 A | 6/1999 | Parins et al. |
| 5,908,429 A | 6/1999 | Yoon |
| 5,911,737 A | 6/1999 | Lee et al. |
| 5,916,146 A | 6/1999 | Allotta et al. |
| 5,916,147 A | 6/1999 | Boury |
| 5,919,207 A | 7/1999 | Taheri |
| 5,921,892 A | 7/1999 | Easton |
| 5,921,993 A | 7/1999 | Yoon |
| 5,921,997 A | 7/1999 | Fogelberg et al. |
| 5,922,008 A | 7/1999 | Gimpelson |
| 5,925,052 A | 7/1999 | Simmons |
| 5,928,255 A | 7/1999 | Meade et al. |
| 5,928,266 A | 7/1999 | Kontos |
| 5,936,536 A | 8/1999 | Morris |
| 5,938,661 A | 8/1999 | Hahnen |
| 5,938,668 A | 8/1999 | Scirica et al. |
| 5,941,815 A | 8/1999 | Chang |
| 5,944,718 A | 8/1999 | Austin et al. |
| 5,951,547 A | 9/1999 | Gough et al. |
| 5,951,549 A | 9/1999 | Richardson et al. |
| 5,954,720 A | 9/1999 | Wilson et al. |
| 5,954,731 A | 9/1999 | Yoon |
| 5,957,936 A | 9/1999 | Yoon et al. |
| 5,957,943 A | 9/1999 | Vaitekunas |
| 5,957,953 A | 9/1999 | DiPoto et al. |
| 5,964,782 A | 10/1999 | Lafontaine et al. |
| 5,970,581 A | 10/1999 | Chadwick et al. |
| 5,971,995 A | 10/1999 | Rousseau |
| 5,972,002 A | 10/1999 | Bark et al. |
| 5,976,074 A | 11/1999 | Moriyama |
| 5,976,075 A | 11/1999 | Beane et al. |
| 5,976,130 A | 11/1999 | McBrayer et al. |
| 5,976,131 A | 11/1999 | Guglielmi et al. |
| 5,980,539 A | 11/1999 | Kontos |
| 5,980,556 A | 11/1999 | Giordano et al. |
| 5,984,933 A | 11/1999 | Yoon |
| 5,984,938 A | 11/1999 | Yoon |
| 5,984,939 A | 11/1999 | Yoon |
| 5,984,950 A | 11/1999 | Cragg et al. |
| 5,989,182 A | 11/1999 | Hori et al. |
| 5,993,447 A | 11/1999 | Blewett et al. |
| 5,993,474 A | 11/1999 | Ouchi |
| 5,995,875 A | 11/1999 | Blewett et al. |
| 5,997,555 A | 12/1999 | Kontos |
| 6,001,120 A | 12/1999 | Levin |
| 6,004,269 A | 12/1999 | Crowley et al. |
| 6,004,330 A | 12/1999 | Middleman et al. |
| 6,007,566 A | 12/1999 | Wenstrom, Jr. |
| 6,010,515 A | 1/2000 | Swain et al. |
| 6,012,494 A | 1/2000 | Balazs |
| 6,016,452 A | 1/2000 | Kasevich |
| 6,017,356 A | 1/2000 | Frederick et al. |
| 6,019,770 A | 2/2000 | Christoudias |
| 6,024,708 A | 2/2000 | Bales et al. |
| 6,024,747 A | 2/2000 | Kontos |
| 6,027,522 A | 2/2000 | Palmer |
| 6,030,365 A | 2/2000 | Laufer |
| 6,030,384 A | 2/2000 | Nezhat |
| 6,030,634 A | 2/2000 | Wu et al. |
| 6,033,399 A | 3/2000 | Gines |
| 6,033,401 A | 3/2000 | Edwards et al. |
| 6,036,640 A | 3/2000 | Corace et al. |
| 6,036,685 A | 3/2000 | Mueller |
| 6,050,992 A | 4/2000 | Nichols |
| 6,053,927 A | 4/2000 | Hamas |
| 6,053,937 A | 4/2000 | Edwards et al. |
| 6,059,719 A | 5/2000 | Yamamoto et al. |
| 6,066,090 A | 5/2000 | Yoon |
| 6,066,160 A | 5/2000 | Colvin et al. |
| 6,068,603 A | 5/2000 | Suzuki |
| 6,068,629 A | 5/2000 | Haissaguerre et al. |
| 6,071,233 A | 6/2000 | Ishikawa et al. |
| 6,074,408 A | 6/2000 | Freeman |
| 6,086,530 A | 7/2000 | Mack |

(56) References Cited

U.S. PATENT DOCUMENTS

| | | | |
|---|---|---|---|
| 6,086,600 A | 7/2000 | Kortenbach |
| 6,090,105 A | 7/2000 | Zepeda et al. |
| 6,090,107 A | 7/2000 | Borgmeier et al. |
| 6,090,108 A | 7/2000 | McBrayer et al. |
| 6,090,129 A | 7/2000 | Ouchi |
| 6,096,046 A | 8/2000 | Weiss |
| 6,102,909 A | 8/2000 | Chen et al. |
| 6,102,926 A | 8/2000 | Tartaglia et al. |
| 6,106,473 A | 8/2000 | Violante et al. |
| 6,106,521 A | 8/2000 | Blewett et al. |
| 6,109,852 A | 8/2000 | Shahinpoor et al. |
| 6,110,154 A | 8/2000 | Shimomura et al. |
| 6,110,183 A | 8/2000 | Cope |
| 6,113,593 A | 9/2000 | Tu et al. |
| 6,117,144 A | 9/2000 | Nobles et al. |
| 6,117,158 A | 9/2000 | Measamer et al. |
| 6,123,701 A | 9/2000 | Nezhat |
| 6,123,718 A | 9/2000 | Tu et al. |
| 6,131,790 A | 10/2000 | Piraka |
| 6,139,555 A | 10/2000 | Hart et al. |
| 6,139,562 A | 10/2000 | Mauze et al. |
| 6,141,037 A | 10/2000 | Upton et al. |
| 6,146,391 A | 11/2000 | Cigaina |
| 6,148,222 A | 11/2000 | Ramsey, III |
| 6,149,653 A | 11/2000 | Deslauriers |
| 6,149,662 A | 11/2000 | Pugliesi et al. |
| 6,152,871 A * | 11/2000 | Foley ............... A61B 17/3417 600/102 |
| 6,152,920 A | 11/2000 | Thompson et al. |
| 6,156,006 A | 12/2000 | Brosens et al. |
| 6,159,200 A | 12/2000 | Verdura et al. |
| 6,165,175 A | 12/2000 | Wampler et al. |
| 6,165,184 A | 12/2000 | Verdura et al. |
| 6,167,297 A | 12/2000 | Benaron |
| 6,168,570 B1 | 1/2001 | Ferrera |
| 6,168,605 B1 | 1/2001 | Measamer et al. |
| 6,169,269 B1 | 1/2001 | Maynard |
| 6,170,130 B1 | 1/2001 | Hamilton et al. |
| 6,173,872 B1 | 1/2001 | Cohen |
| 6,179,776 B1 | 1/2001 | Adams et al. |
| 6,179,832 B1 | 1/2001 | Jones et al. |
| 6,179,837 B1 | 1/2001 | Hooven |
| 6,183,420 B1 | 2/2001 | Douk et al. |
| 6,183,469 B1 | 2/2001 | Thapliyal et al. |
| 6,187,026 B1 * | 2/2001 | Devlin ............... A61B 17/2909 606/205 |
| 6,190,353 B1 | 2/2001 | Makower et al. |
| 6,190,383 B1 | 2/2001 | Schmaltz et al. |
| 6,190,384 B1 | 2/2001 | Ouchi |
| 6,190,399 B1 | 2/2001 | Palmer et al. |
| 6,203,533 B1 | 3/2001 | Ouchi |
| 6,206,872 B1 | 3/2001 | Lafond et al. |
| 6,206,877 B1 | 3/2001 | Kese et al. |
| 6,206,904 B1 | 3/2001 | Ouchi |
| 6,210,409 B1 | 4/2001 | Ellman et al. |
| 6,214,007 B1 | 4/2001 | Anderson |
| 6,214,028 B1 | 4/2001 | Yoon et al. |
| 6,216,043 B1 | 4/2001 | Swanson et al. |
| 6,228,096 B1 | 5/2001 | Marchand |
| 6,231,506 B1 | 5/2001 | Hu et al. |
| 6,234,958 B1 | 5/2001 | Snoke et al. |
| 6,240,312 B1 | 5/2001 | Alfano et al. |
| 6,245,079 B1 | 6/2001 | Nobles et al. |
| 6,246,914 B1 | 6/2001 | de la Rama et al. |
| 6,248,124 B1 | 6/2001 | Pedros et al. |
| 6,258,064 B1 | 7/2001 | Smith et al. |
| 6,261,242 B1 | 7/2001 | Roberts et al. |
| 6,264,664 B1 | 7/2001 | Avellanet |
| 6,270,497 B1 | 8/2001 | Sekino et al. |
| 6,270,505 B1 | 8/2001 | Yoshida et al. |
| 6,277,136 B1 | 8/2001 | Bonutti |
| 6,280,379 B1 | 8/2001 | Resnick |
| 6,283,963 B1 | 9/2001 | Regula |
| 6,287,304 B1 | 9/2001 | Eggers et al. |
| 6,293,909 B1 | 9/2001 | Chu et al. |
| 6,293,952 B1 | 9/2001 | Brosens et al. |
| 6,296,630 B1 | 10/2001 | Altman et al. |
| 6,306,131 B1 | 10/2001 | Hareyama et al. |
| 6,306,159 B1 | 10/2001 | Schwartz et al. |
| 6,314,963 B1 | 11/2001 | Vaska et al. |
| 6,322,578 B1 | 11/2001 | Houle et al. |
| 6,325,534 B1 | 12/2001 | Hawley et al. |
| 6,326,177 B1 | 12/2001 | Schoenbach et al. |
| 6,328,730 B1 | 12/2001 | Harkrider, Jr. |
| 6,346,092 B1 | 2/2002 | Leschlnsky |
| 6,350,267 B1 | 2/2002 | Stefanchik |
| 6,350,269 B1 | 2/2002 | Shipp et al. |
| 6,350,278 B1 | 2/2002 | Lenker et al. |
| 6,352,503 B1 | 3/2002 | Matsui et al. |
| 6,352,541 B1 | 3/2002 | Kienzle et al. |
| 6,352,543 B1 | 3/2002 | Cole |
| 6,355,013 B1 | 3/2002 | van Muiden |
| 6,355,035 B1 | 3/2002 | Manushakian |
| 6,361,534 B1 | 3/2002 | Chen et al. |
| 6,364,879 B1 | 4/2002 | Chen et al. |
| 6,368,340 B2 | 4/2002 | Malecki et al. |
| 6,371,956 B1 | 4/2002 | Wlson et al. |
| 6,379,366 B1 | 4/2002 | Fleischman et al. |
| 6,383,195 B1 | 5/2002 | Richard |
| 6,383,197 B1 | 5/2002 | Conlon et al. |
| 6,387,671 B1 | 5/2002 | Rubinsky et al. |
| 6,391,029 B1 | 5/2002 | Hooven et al. |
| 6,398,708 B1 | 6/2002 | Hastings et al. |
| 6,402,735 B1 | 6/2002 | Langevin |
| 6,402,746 B1 | 6/2002 | Whayne et al. |
| 6,406,440 B1 | 6/2002 | Stefanchik |
| 6,409,727 B1 | 6/2002 | Bales et al. |
| 6,409,733 B1 | 6/2002 | Conlon et al. |
| 6,419,639 B2 | 7/2002 | Walther et al. |
| 6,419,641 B1 | 7/2002 | Mark et al. |
| 6,427,089 B1 | 7/2002 | Knowlton |
| 6,431,500 B1 | 8/2002 | Jacobs et al. |
| 6,436,107 B1 | 8/2002 | Wang et al. |
| 6,443,970 B1 | 9/2002 | Schulze et al. |
| 6,443,988 B2 | 9/2002 | Felt et al. |
| 6,447,444 B1 | 9/2002 | Avni et al. |
| 6,447,511 B1 | 9/2002 | Slater |
| 6,447,523 B1 | 9/2002 | Middleman et al. |
| 6,454,783 B1 | 9/2002 | Piskun |
| 6,454,785 B2 | 9/2002 | De Hoyos Garza |
| 6,458,074 B1 | 10/2002 | Matsui et al. |
| 6,458,076 B1 | 10/2002 | Pruitt |
| 6,464,697 B1 | 10/2002 | Edwards et al. |
| 6,464,701 B1 | 10/2002 | Hooven et al. |
| 6,464,702 B2 | 10/2002 | Schulze et al. |
| 6,470,218 B1 | 10/2002 | Behl |
| 6,475,104 B1 | 11/2002 | Lutz et al. |
| 6,485,411 B1 | 11/2002 | Konstorum et al. |
| 6,489,745 B1 | 12/2002 | Koreis |
| 6,491,626 B1 | 12/2002 | Stone et al. |
| 6,491,627 B1 | 12/2002 | Komi |
| 6,491,691 B1 | 12/2002 | Morley et al. |
| 6,493,590 B1 | 12/2002 | Wessman et al. |
| 6,494,893 B2 | 12/2002 | Dubrul et al. |
| 6,500,176 B1 | 12/2002 | Truckai et al. |
| 6,503,192 B1 | 1/2003 | Ouchi |
| 6,506,190 B1 | 1/2003 | Walshe |
| 6,508,827 B1 | 1/2003 | Manhes |
| 6,514,239 B2 | 2/2003 | Shlmmura et al. |
| 6,516,500 B2 | 2/2003 | Ogino et al. |
| 6,517,534 B1 | 2/2003 | McGovern et al. |
| 6,520,954 B2 | 2/2003 | Ouchi |
| 6,526,320 B2 | 2/2003 | Mitchell |
| 6,527,753 B2 | 3/2003 | Sekine et al. |
| 6,527,782 B2 | 3/2003 | Hogg et al. |
| 6,530,880 B2 | 3/2003 | Pagliuca |
| 6,530,922 B2 | 3/2003 | Cosman et al. |
| 6,535,764 B2 | 3/2003 | Imran et al. |
| 6,537,200 B2 | 3/2003 | Leysieffer et al. |
| 6,543,456 B1 | 4/2003 | Freeman |
| 6,551,270 B1 | 4/2003 | Bimbo et al. |
| 6,551,356 B2 | 4/2003 | Rousseau |
| 6,554,766 B2 | 4/2003 | Maeda et al. |
| 6,554,823 B2 | 4/2003 | Palmer et al. |

(56) References Cited

U.S. PATENT DOCUMENTS

| | | |
|---|---|---|
| 6,554,829 B2 | 4/2003 | Schulze et al. |
| 6,558,384 B2 | 5/2003 | Mayenberger |
| 6,562,034 B2 | 5/2003 | Edwards et al. |
| 6,562,035 B1 | 5/2003 | Levin |
| 6,562,052 B2 | 5/2003 | Nobles et al. |
| 6,569,085 B2 | 5/2003 | Kortenbach et al. |
| 6,569,091 B2 | 5/2003 | Diokno et al. |
| 6,569,120 B1 | 5/2003 | Green et al. |
| 6,569,159 B1 | 5/2003 | Edwards et al. |
| 6,572,629 B2 | 6/2003 | Kalloo et al. |
| 6,572,635 B1 | 6/2003 | Bonutti |
| 6,575,988 B2 | 6/2003 | Rousseau |
| 6,579,311 B1 | 6/2003 | Makower |
| 6,581,889 B2 | 6/2003 | Carpenter et al. |
| 6,585,642 B2 | 7/2003 | Christopher |
| 6,585,717 B1 | 7/2003 | Wittenberger et al. |
| 6,587,750 B2 | 7/2003 | Gerbi et al. |
| 6,592,559 B1 | 7/2003 | Pakter et al. |
| 6,592,603 B2 | 7/2003 | Lasner |
| 6,594,971 B1 | 7/2003 | Addy et al. |
| 6,602,262 B2 | 8/2003 | Griego et al. |
| 6,605,105 B1 | 8/2003 | Cuschieri et al. |
| 6,607,529 B1 | 8/2003 | Jones et al. |
| 6,610,072 B1 | 8/2003 | Christy et al. |
| 6,610,074 B2 | 8/2003 | Santilli |
| 6,613,038 B2 | 9/2003 | Bonutti et al. |
| 6,613,068 B2 | 9/2003 | Ouchi |
| 6,616,632 B2 | 9/2003 | Sharp et al. |
| 6,620,193 B1 | 9/2003 | Lau et al. |
| 6,623,448 B2 | 9/2003 | Slater |
| 6,626,919 B1 | 9/2003 | Swanstrom |
| 6,632,171 B2 | 10/2003 | Iddan et al. |
| 6,632,229 B1 | 10/2003 | Yamanouchi |
| 6,632,234 B2 | 10/2003 | Kieturakis et al. |
| 6,638,275 B1 | 10/2003 | McGaffigan et al. |
| 6,638,286 B1 | 10/2003 | Burbank et al. |
| 6,645,225 B1 | 11/2003 | Atkinson |
| 6,652,518 B2 | 11/2003 | Wellman et al. |
| 6,652,521 B2 | 11/2003 | Schulze |
| 6,652,545 B2 | 11/2003 | Shipp et al. |
| 6,652,551 B1 | 11/2003 | Heiss |
| 6,656,194 B1 | 12/2003 | Gannoe et al. |
| 6,662,035 B2 | 12/2003 | Sochor |
| 6,663,641 B1 | 12/2003 | Kovac et al. |
| 6,663,655 B2 | 12/2003 | Ginn et al. |
| 6,666,854 B1 | 12/2003 | Lange |
| 6,672,338 B1 | 1/2004 | Esashi et al. |
| 6,673,058 B2 | 1/2004 | Snow |
| 6,673,070 B2 | 1/2004 | Edwards et al. |
| 6,673,087 B1 | 1/2004 | Chang et al. |
| 6,673,092 B1 | 1/2004 | Bacher |
| 6,676,685 B2 | 1/2004 | Pedros et al. |
| 6,679,882 B1 | 1/2004 | Kornerup |
| 6,684,938 B2 | 2/2004 | Tsujita et al. |
| 6,685,628 B2 | 2/2004 | Vu |
| 6,685,724 B1 | 2/2004 | Haluck |
| 6,692,445 B2 | 2/2004 | Roberts et al. |
| 6,692,462 B2 | 2/2004 | Mackenzie et al. |
| 6,692,493 B2 | 2/2004 | McGovern et al. |
| 6,695,867 B2 | 2/2004 | Ginn et al. |
| 6,699,180 B2 | 3/2004 | Kobayashi |
| 6,699,256 B1 | 3/2004 | Logan et al. |
| 6,699,263 B2 | 3/2004 | Cope |
| 6,706,018 B2 | 3/2004 | Westlund et al. |
| 6,708,066 B2 | 3/2004 | Herbst et al. |
| 6,709,188 B2 | 3/2004 | Ushimaru |
| 6,709,445 B2 | 3/2004 | Boebel et al. |
| 6,716,226 B2 | 4/2004 | Sixto, Jr. et al. |
| 6,731,875 B1 | 5/2004 | Kartalopoulos |
| 6,736,822 B2 | 5/2004 | McClellan et al. |
| 6,740,030 B2 | 5/2004 | Martone et al. |
| 6,740,082 B2 | 5/2004 | Shadduck |
| 6,743,166 B2 | 6/2004 | Berci et al. |
| 6,743,226 B2 | 6/2004 | Cosman et al. |
| 6,743,239 B1 | 6/2004 | Kuehn et al. |
| 6,743,240 B2 | 6/2004 | Smith et al. |
| 6,749,560 B1 | 6/2004 | Konstorum et al. |
| 6,749,609 B1 | 6/2004 | Lunsford et al. |
| 6,752,768 B2 | 6/2004 | Burdorff et al. |
| 6,752,811 B2 | 6/2004 | Chu et al. |
| 6,752,822 B2 | 6/2004 | Jespersen |
| 6,758,857 B2 | 7/2004 | Cloanta et al. |
| 6,761,685 B2 | 7/2004 | Adams et al. |
| 6,761,718 B2 | 7/2004 | Madsen |
| 6,761,722 B2 | 7/2004 | Cole et al. |
| 6,767,352 B2 | 7/2004 | Field et al. |
| 6,767,356 B2 | 7/2004 | Kanner et al. |
| 6,773,434 B2 | 8/2004 | Ciarrocca |
| 6,776,165 B2 | 8/2004 | Jin |
| 6,776,787 B2 | 8/2004 | Phung et al. |
| 6,780,151 B2 | 8/2004 | Grabover et al. |
| 6,780,352 B2 | 8/2004 | Jacobson |
| 6,783,491 B2 | 8/2004 | Saadat et al. |
| 6,786,382 B1 | 9/2004 | Hoffman |
| 6,786,864 B2 | 9/2004 | Matsuura et al. |
| 6,786,905 B2 | 9/2004 | Swanson et al. |
| 6,788,977 B2 | 9/2004 | Fenn et al. |
| 6,790,173 B2 | 9/2004 | Saadat et al. |
| 6,790,217 B2 | 9/2004 | Schulze et al. |
| 6,795,728 B2 | 9/2004 | Chornenky et al. |
| 6,800,056 B2 | 10/2004 | Tartaglia et al. |
| 6,808,491 B2 | 10/2004 | Kortenbach et al. |
| 6,814,697 B2 | 11/2004 | Ouchi |
| 6,814,739 B2 | 11/2004 | Secrest et al. |
| 6,817,974 B2 | 11/2004 | Cooper et al. |
| 6,818,007 B1 | 11/2004 | Dampney et al. |
| 6,821,285 B2 | 11/2004 | Laufer et al. |
| 6,824,548 B2 | 11/2004 | Smith et al. |
| 6,830,545 B2 | 12/2004 | Bendall |
| 6,830,578 B2 | 12/2004 | O'Heeron et al. |
| 6,835,200 B2 | 12/2004 | Laufer et al. |
| 6,836,688 B2 | 12/2004 | Ingle et al. |
| 6,837,847 B2 | 1/2005 | Ewers et al. |
| 6,837,886 B2 | 1/2005 | Collins et al. |
| 6,840,246 B2 | 1/2005 | Downing |
| 6,840,938 B1 | 1/2005 | Morley et al. |
| 6,843,794 B2 | 1/2005 | Sixto, Jr. et al. |
| 6,852,078 B2 | 2/2005 | Ouchi |
| 6,861,250 B1 | 3/2005 | Cole et al. |
| 6,866,627 B2 | 3/2005 | Nozue |
| 6,866,628 B2 | 3/2005 | Goodman et al. |
| 6,869,394 B2 | 3/2005 | Ishibiki |
| 6,869,395 B2 | 3/2005 | Page et al. |
| 6,869,398 B2 | 3/2005 | Obenchain et al. |
| 6,878,106 B1 | 4/2005 | Herrmann |
| 6,878,110 B2 | 4/2005 | Yang et al. |
| 6,881,213 B2 | 4/2005 | Ryan et al. |
| 6,881,216 B2 | 4/2005 | Di Caprio et al. |
| 6,884,213 B2 | 4/2005 | Raz et al. |
| 6,887,255 B2 | 5/2005 | Shimm |
| 6,889,089 B2 | 5/2005 | Behl et al. |
| 6,890,295 B2 | 5/2005 | Michels et al. |
| 6,896,683 B1 | 5/2005 | Gadberry et al. |
| 6,896,692 B2 | 5/2005 | Ginn et al. |
| 6,899,710 B2 | 5/2005 | Hooven |
| 6,908,427 B2 | 6/2005 | Fleener et al. |
| 6,908,476 B2 | 6/2005 | Jud et al. |
| 6,911,019 B2 | 6/2005 | Mulier et al. |
| 6,913,613 B2 | 7/2005 | Schwarz et al. |
| 6,916,284 B2 | 7/2005 | Moriyama |
| 6,918,871 B2 | 7/2005 | Schulze |
| 6,918,906 B2 | 7/2005 | Long |
| 6,918,908 B2 | 7/2005 | Bonner et al. |
| 6,921,408 B2 | 7/2005 | Sauer |
| 6,926,723 B1 | 8/2005 | Mulhauser et al. |
| 6,926,725 B2 | 8/2005 | Cooke et al. |
| 6,932,810 B2 | 8/2005 | Ryan |
| 6,932,824 B1 | 8/2005 | Roop et al. |
| 6,932,827 B2 | 8/2005 | Cole |
| 6,932,834 B2 | 8/2005 | Lizard et al. |
| 6,936,003 B2 | 8/2005 | Iddan |
| 6,939,290 B2 | 9/2005 | Iddan |
| 6,939,292 B2 | 9/2005 | Mizuno |
| 6,939,327 B2 | 9/2005 | Hall et al. |

(56) References Cited

U.S. PATENT DOCUMENTS

| | | |
|---|---|---|
| 6,939,347 B2 | 9/2005 | Thompson |
| 6,942,613 B2 | 9/2005 | Ewers et al. |
| 6,944,490 B1 | 9/2005 | Chow |
| 6,945,472 B2 | 9/2005 | Wuttke et al. |
| 6,945,979 B2 | 9/2005 | Kortenbach et al. |
| 6,949,096 B2 | 9/2005 | Davison et al. |
| 6,949,105 B2 | 9/2005 | Bryan et al. |
| 6,955,641 B2 | 10/2005 | Lubock |
| 6,955,683 B2 | 10/2005 | Bonutti |
| 6,958,035 B2 | 10/2005 | Friedman et al. |
| 6,960,162 B2 | 11/2005 | Saadat et al. |
| 6,960,163 B2 | 11/2005 | Ewers et al. |
| 6,960,183 B2 | 11/2005 | Nicolette |
| 6,962,587 B2 | 11/2005 | Johnson et al. |
| 6,964,662 B2 | 11/2005 | Kidooka |
| 6,966,909 B2 | 11/2005 | Marshall et al. |
| 6,966,919 B2 | 11/2005 | Sixto, Jr. et al. |
| 6,967,462 B1 | 11/2005 | Landis |
| 6,971,988 B2 | 12/2005 | Orban, III |
| 6,972,017 B2 | 12/2005 | Smith et al. |
| 6,974,411 B2 | 12/2005 | Belson |
| 6,976,992 B2 | 12/2005 | Sachatello et al. |
| 6,980,854 B2 | 12/2005 | Bernabe! |
| 6,980,858 B2 | 12/2005 | Fuimaono et al. |
| 6,984,205 B2 | 1/2006 | Gazdzinskl |
| 6,986,738 B2 | 1/2006 | Glukhovsky et al. |
| 6,986,774 B2 | 1/2006 | Middleman et al. |
| 6,988,987 B2 | 1/2006 | Ishikawa et al. |
| 6,989,028 B2 | 1/2006 | Lashinski et al. |
| 6,991,602 B2 | 1/2006 | Nakazawa et al. |
| 6,991,627 B2 | 1/2006 | Madhani et al. |
| 6,991,631 B2 | 1/2006 | Woloszko et al. |
| 6,994,705 B2 | 2/2006 | Nobis et al. |
| 6,994,706 B2 | 2/2006 | Chornenky et al. |
| 6,994,708 B2 | 2/2006 | Manzo |
| 6,997,870 B2 | 2/2006 | Couvillon, Jr. |
| 6,997,931 B2 | 2/2006 | Sauer et al. |
| 7,000,818 B2 | 2/2006 | Shelton, IV et al. |
| 7,001,329 B2 | 2/2006 | Kobayashi et al. |
| 7,001,341 B2 | 2/2006 | Gellman et al. |
| 7,004,957 B1 | 2/2006 | Dampney et al. |
| 7,008,375 B2 | 3/2006 | Weisel |
| 7,008,419 B2 | 3/2006 | Shadduck |
| 7,009,634 B2 | 3/2006 | Iddan et al. |
| 7,010,340 B2 | 3/2006 | Scarantlno et al. |
| 7,011,669 B2 | 3/2006 | Kimblad |
| 7,018,373 B2 | 3/2006 | Suzuki |
| 7,020,531 B1 | 3/2006 | Colliou et al. |
| 7,025,580 B2 | 4/2006 | Heagy et al. |
| 7,025,721 B2 | 4/2006 | Cohen et al. |
| 7,029,435 B2 | 4/2006 | Nakao |
| 7,029,438 B2 | 4/2006 | Morin et al. |
| 7,029,450 B2 | 4/2006 | Gellman |
| 7,032,600 B2 | 4/2006 | Fukuda et al. |
| 7,035,680 B2 | 4/2006 | Partridge et al. |
| 7,037,290 B2 | 5/2006 | Gardeski et al. |
| 7,041,052 B2 | 5/2006 | Saadat et al. |
| 7,052,454 B2 | 5/2006 | Taylor |
| 7,052,489 B2 | 5/2006 | Griego et al. |
| 7,056,330 B2 | 6/2006 | Gayton |
| 7,060,024 B2 | 6/2006 | Long et al. |
| 7,060,025 B2 | 6/2006 | Long et al. |
| 7,063,697 B2 | 6/2006 | Slater |
| 7,063,715 B2 | 6/2006 | Onuki et al. |
| 7,066,879 B2 | 6/2006 | Fowler et al. |
| 7,066,936 B2 | 6/2006 | Ryan |
| 7,070,559 B2 | 7/2006 | Adams et al. |
| 7,070,602 B2 | 7/2006 | Smith et al. |
| 7,076,305 B2 | 7/2006 | Imran et al. |
| 7,083,618 B2 | 8/2006 | Couture et al. |
| 7,083,620 B2 | 8/2006 | Jahns et al. |
| 7,083,629 B2 | 8/2006 | Weller et al. |
| 7,083,635 B2 | 8/2006 | Ginn |
| 7,087,010 B2 | 8/2006 | Ootawara et al. |
| 7,087,071 B2 | 8/2006 | Nicholas et al. |
| 7,088,923 B2 | 8/2006 | Haruyama |
| 7,090,673 B2 | 8/2006 | Dycus et al. |
| 7,090,683 B2 | 8/2006 | Brock et al. |
| 7,090,685 B2 | 8/2006 | Kortenbach et al. |
| 7,093,518 B2 | 8/2006 | Gmeilbauer |
| 7,101,371 B2 | 9/2006 | Dycus et al. |
| 7,101,372 B2 | 9/2006 | Dycus et al. |
| 7,101,373 B2 | 9/2006 | Dycus et al. |
| 7,105,000 B2 | 9/2006 | McBrayer |
| 7,105,005 B2 | 9/2006 | Blake |
| 7,108,696 B2 | 9/2006 | Daniel et al. |
| 7,108,703 B2 | 9/2006 | Danitz et al. |
| 7,112,208 B2 | 9/2006 | Morris et al. |
| 7,115,092 B2 | 10/2006 | Park et al. |
| 7,115,124 B1 | 10/2006 | Xiao |
| 7,115,785 B2 | 10/2006 | Guggenheim et al. |
| 7,117,703 B2 | 10/2006 | Kato et al. |
| 7,118,531 B2 | 10/2006 | Krill |
| 7,118,578 B2 | 10/2006 | West, Jr. et al. |
| 7,118,587 B2 | 10/2006 | Dycus et al. |
| 7,122,605 B2 | 10/2006 | Ohrbom et al. |
| 7,128,708 B2 | 10/2006 | Saadat et al. |
| 7,130,697 B2 | 10/2006 | Chornenky et al. |
| RE39,415 E | 11/2006 | Bales et al. |
| 7,131,978 B2 | 11/2006 | Sancoff et al. |
| 7,131,979 B2 | 11/2006 | DiCarlo et al. |
| 7,131,980 B1 | 11/2006 | Field et al. |
| 7,137,980 B2 | 11/2006 | Buysse et al. |
| 7,137,981 B2 | 11/2006 | Long |
| 7,146,984 B2 | 12/2006 | Stack et al. |
| 7,147,650 B2 | 12/2006 | Lee |
| 7,150,097 B2 | 12/2006 | Sremcich et al. |
| 7,150,655 B2 | 12/2006 | Mastrototaro et al. |
| 7,150,713 B2 | 12/2006 | Shener et al. |
| 7,150,750 B2 | 12/2006 | Damarati |
| 7,152,488 B2 | 12/2006 | Hedrich et al. |
| 7,153,321 B2 | 12/2006 | Andrews |
| 7,156,845 B2 | 1/2007 | Mulier et al. |
| 7,160,296 B2 | 1/2007 | Pearson et al. |
| 7,163,525 B2 | 1/2007 | Franer |
| 7,169,104 B2 | 1/2007 | Ueda et al. |
| 7,169,115 B2 | 1/2007 | Nobis et al. |
| 7,172,714 B2 | 2/2007 | Jacobson |
| 7,175,591 B2 | 2/2007 | Kaladelfos |
| 7,179,254 B2 | 2/2007 | Pendekanti et al. |
| 7,179,262 B2 | 2/2007 | Bryan et al. |
| 7,186,265 B2 | 3/2007 | Sharkawy et al. |
| 7,188,627 B2 | 3/2007 | Nelson et al. |
| 7,189,231 B2 | 3/2007 | Clague et al. |
| 7,195,612 B2 | 3/2007 | van Sloten et al. |
| 7,195,631 B2 | 3/2007 | Dumbauld |
| 7,204,804 B2 | 4/2007 | Zirps et al. |
| 7,204,820 B2 | 4/2007 | Akahoshi |
| 7,204,840 B2 | 4/2007 | Skakoon et al. |
| 7,207,997 B2 | 4/2007 | Shipp et al. |
| 7,208,005 B2 | 4/2007 | Frecker et al. |
| 7,211,089 B2 | 5/2007 | Kear et al. |
| 7,211,092 B2 | 5/2007 | Hughett |
| 7,220,227 B2 | 5/2007 | Sasaki et al. |
| 7,223,271 B2 | 5/2007 | Muramatsu et al. |
| 7,223,272 B2 | 5/2007 | Francese et al. |
| 7,226,458 B2 | 6/2007 | Kaplan et al. |
| 7,229,438 B2 | 6/2007 | Young |
| 7,232,414 B2 | 6/2007 | Gonzalez |
| 7,232,445 B2 | 6/2007 | Kortenbach et al. |
| 7,235,084 B2 | 6/2007 | Skakoon et al. |
| 7,235,089 B1 | 6/2007 | McGuckin, Jr. |
| 7,241,290 B2 | 7/2007 | Doyle et al. |
| 7,241,295 B2 | 7/2007 | Maguire |
| 7,244,228 B2 | 7/2007 | Bowski |
| 7,250,027 B2 | 7/2007 | Barry |
| 7,252,660 B2 | 8/2007 | Kunz |
| 7,255,675 B2 | 8/2007 | Gertner et al. |
| 7,261,725 B2 | 8/2007 | Binmoeller |
| 7,261,728 B2 | 8/2007 | Long et al. |
| 7,270,663 B2 | 9/2007 | Nakao |
| 7,278,179 B2 | 10/2007 | Schneider |
| 7,288,075 B2 | 10/2007 | Parihar et al. |
| 7,290,615 B2 | 11/2007 | Christanti et al. |

(56) References Cited

U.S. PATENT DOCUMENTS

| | | |
|---|---|---|
| 7,291,127 B2 | 11/2007 | Eidenschink |
| 7,294,139 B1 | 11/2007 | Gengler |
| 7,301,250 B2 | 11/2007 | Cassel |
| 7,306,597 B2 | 12/2007 | Manzo |
| 7,308,828 B2 | 12/2007 | Hashimoto |
| 7,311,107 B2 | 12/2007 | Harel et al. |
| 7,318,802 B2 | 1/2008 | Suzuki et al. |
| 7,320,695 B2 | 1/2008 | Carroll |
| 7,322,934 B2 | 1/2008 | Miyake et al. |
| 7,323,006 B2 | 1/2008 | Andreas et al. |
| 7,329,256 B2 | 2/2008 | Johnson et al. |
| 7,329,257 B2 | 2/2008 | Kanehira et al. |
| 7,329,383 B2 | 2/2008 | Stinson |
| 7,331,968 B2 | 2/2008 | Arp et al. |
| 7,335,220 B2 | 2/2008 | Khosravi et al. |
| 7,338,513 B2 | 3/2008 | Lee et al. |
| 7,341,554 B2 | 3/2008 | Sekine et al. |
| 7,344,536 B1 | 3/2008 | Lunsford et al. |
| 7,349,223 B2 | 3/2008 | Haemer et al. |
| 7,352,387 B2 | 4/2008 | Yamamoto |
| 7,357,802 B2 | 4/2008 | Palanker et al. |
| 7,357,806 B2 | 4/2008 | Rivera et al. |
| 7,364,582 B2 | 4/2008 | Lee |
| 7,367,939 B2 | 5/2008 | Smith et al. |
| 7,371,215 B2 | 5/2008 | Colliou et al. |
| 7,381,216 B2 | 6/2008 | Buzzard et al. |
| 7,390,324 B2 | 6/2008 | Whalen et al. |
| 7,393,322 B2 | 7/2008 | Wenchell |
| 7,402,162 B2 | 7/2008 | Ouchi |
| 7,404,791 B2 | 7/2008 | Linares et al. |
| 7,410,483 B2 | 8/2008 | Danitz et al. |
| 7,413,563 B2 | 8/2008 | Corcoran et al. |
| 7,416,554 B2 | 8/2008 | Lam et al. |
| 7,422,590 B2 | 9/2008 | Kupferschmid et al. |
| 7,431,694 B2 | 10/2008 | Stefanchik et al. |
| 7,435,229 B2 | 10/2008 | Wolf |
| 7,435,257 B2 | 10/2008 | Lashinski et al. |
| 7,441,507 B2 | 10/2008 | Teraura et al. |
| 7,442,166 B2 | 10/2008 | Huang et al. |
| 7,452,327 B2 | 11/2008 | Durgin et al. |
| 7,455,208 B2 | 11/2008 | Wales et al. |
| 7,455,675 B2 | 11/2008 | Schur et al. |
| 7,468,066 B2 | 12/2008 | Vargas et al. |
| 7,476,237 B2 | 1/2009 | Taniguchi et al. |
| 7,479,104 B2 | 1/2009 | Lau et al. |
| 7,485,093 B2 | 2/2009 | Glukhovsky |
| 7,488,295 B2 | 2/2009 | Burbank et al. |
| 7,494,499 B2 | 2/2009 | Nagase et al. |
| 7,497,867 B2 | 3/2009 | Lasner et al. |
| 7,498,950 B1 | 3/2009 | Ertas et al. |
| 7,507,200 B2 | 3/2009 | Okada |
| 7,507,239 B2 | 3/2009 | Shadduck |
| 7,510,107 B2 | 3/2009 | Timm et al. |
| 7,511,733 B2 | 3/2009 | Takizawa et al. |
| 7,514,568 B2 | 4/2009 | Freeman |
| 7,515,953 B2 | 4/2009 | Madar et al. |
| 7,520,876 B2 | 4/2009 | Ressemann et al. |
| 7,520,950 B2 | 4/2009 | Saadat et al. |
| 7,524,281 B2 | 4/2009 | Chu et al. |
| 7,524,302 B2 | 4/2009 | Tower |
| 7,534,228 B2 | 5/2009 | Wiliams |
| 7,535,570 B2 | 5/2009 | Muraishi |
| 7,536,217 B2 | 5/2009 | Minai et al. |
| 7,540,872 B2 | 6/2009 | Schechter et al. |
| 7,542,807 B2 | 6/2009 | Bertolero et al. |
| 7,544,195 B2 | 6/2009 | Lunsford et al. |
| 7,544,203 B2 | 6/2009 | Chin et al. |
| 7,547,310 B2 | 6/2009 | Whitfield |
| 7,548,040 B2 | 6/2009 | Lee et al. |
| 7,549,564 B2 | 6/2009 | Boudreaux |
| 7,549,990 B2 | 6/2009 | Canady |
| 7,549,991 B2 | 6/2009 | Lu et al. |
| 7,549,998 B2 | 6/2009 | Braun |
| 7,553,278 B2 | 6/2009 | Kucklick |
| 7,553,298 B2 | 6/2009 | Hunt et al. |
| 7,559,452 B2 | 7/2009 | Wales et al. |
| 7,559,887 B2 | 7/2009 | Dannan |
| 7,559,916 B2 | 7/2009 | Smith et al. |
| 7,560,006 B2 | 7/2009 | Rakos et al. |
| 7,561,907 B2 | 7/2009 | Fuimaono et al. |
| 7,561,916 B2 | 7/2009 | Hunt et al. |
| 7,565,201 B2 | 7/2009 | Blackmore et al. |
| 7,566,334 B2 | 7/2009 | Christian et al. |
| 7,575,144 B2 | 8/2009 | Ortiz et al. |
| 7,575,548 B2 | 8/2009 | Takemoto et al. |
| 7,578,832 B2 | 8/2009 | Johnson et al. |
| 7,579,005 B2 | 8/2009 | Keeler et al. |
| 7,579,550 B2 | 8/2009 | Dayton et al. |
| 7,582,096 B2 | 9/2009 | Gellman et al. |
| 7,588,177 B2 | 9/2009 | Racenet |
| 7,588,557 B2 | 9/2009 | Nakao |
| 7,588,585 B2 | 9/2009 | Gold et al. |
| 7,591,781 B2 | 9/2009 | Hirata |
| 7,591,783 B2 | 9/2009 | Boulais et al. |
| 7,597,229 B2 | 10/2009 | Boudreaux et al. |
| 7,604,150 B2 | 10/2009 | Boudreaux |
| 7,604,633 B2 | 10/2009 | Truckai et al. |
| 7,608,083 B2 | 10/2009 | Lee et al. |
| 7,611,479 B2 | 11/2009 | Cragg et al. |
| 7,612,084 B2 | 11/2009 | James et al. |
| 7,615,002 B2 | 11/2009 | Rothweiler et al. |
| 7,615,003 B2 | 11/2009 | Stefanchik et al. |
| 7,615,005 B2 | 11/2009 | Stefanchik et al. |
| 7,615,058 B2 | 11/2009 | Sixto, Jr. et al. |
| 7,615,067 B2 | 11/2009 | Lee et al. |
| 7,618,398 B2 | 11/2009 | Holman et al. |
| 7,618,437 B2 | 11/2009 | Nakao |
| 7,621,910 B2 | 11/2009 | Sugi |
| 7,621,927 B2 | 11/2009 | Messerly et al. |
| 7,621,936 B2 | 11/2009 | Cragg et al. |
| 7,628,792 B2 | 12/2009 | Guerra |
| 7,628,797 B2 | 12/2009 | Tieu et al. |
| 7,632,250 B2 | 12/2009 | Smith et al. |
| 7,635,373 B2 | 12/2009 | Ortiz |
| 7,637,903 B2 | 12/2009 | Lentz et al. |
| 7,637,905 B2 | 12/2009 | Saadat et al. |
| 7,645,288 B2 | 1/2010 | McKenna et al. |
| 7,648,457 B2 | 1/2010 | Stefanchik et al. |
| 7,648,519 B2 | 1/2010 | Lee et al. |
| 7,650,742 B2 | 1/2010 | Ushijima |
| 7,651,483 B2 | 1/2010 | Byrum et al. |
| 7,651,509 B2 | 1/2010 | Bojarski et al. |
| 7,653,438 B2 | 1/2010 | Deem et al. |
| 7,654,431 B2 | 2/2010 | Hueil et al. |
| 7,655,004 B2 | 2/2010 | Long |
| 7,658,738 B2 | 2/2010 | Nobis et al. |
| 7,662,089 B2 | 2/2010 | Okada et al. |
| 7,666,180 B2 | 2/2010 | Holsten et al. |
| 7,666,203 B2 | 2/2010 | Chanduszko et al. |
| 7,670,282 B2 | 3/2010 | Mathis |
| 7,670,336 B2 | 3/2010 | Young et al. |
| 7,670,346 B2 | 3/2010 | Whitfield |
| 7,674,259 B2 | 3/2010 | Shadduck |
| 7,674,275 B2 | 3/2010 | Martin et al. |
| 7,678,043 B2 | 3/2010 | Gilad |
| 7,680,543 B2 | 3/2010 | Azure |
| 7,684,599 B2 | 3/2010 | Horn et al. |
| 7,684,851 B2 | 3/2010 | Miyake et al. |
| 7,686,826 B2 | 3/2010 | Lee et al. |
| 7,691,103 B2 | 4/2010 | Fernandez et al. |
| 7,697,970 B2 | 4/2010 | Uchiyama et al. |
| 7,699,835 B2 | 4/2010 | Lee et al. |
| 7,699,864 B2 | 4/2010 | Kick et al. |
| 7,704,248 B2 | 4/2010 | DiCarlo |
| 7,708,756 B2 | 5/2010 | Nobis et al. |
| 7,710,563 B2 | 5/2010 | Betzig et al. |
| 7,713,189 B2 | 5/2010 | Hanke |
| 7,713,270 B2 | 5/2010 | Suzuki |
| 7,717,847 B2 | 5/2010 | Smith |
| 7,721,742 B2 | 5/2010 | Kalloo et al. |
| 7,722,631 B2 | 5/2010 | Mikkaichi et al. |
| 7,727,242 B2 | 6/2010 | Sepetka et al. |
| 7,727,246 B2 | 6/2010 | Sixto, Jr. et al. |
| 7,727,248 B2 | 6/2010 | Smith et al. |

(56) References Cited

U.S. PATENT DOCUMENTS

| | | |
|---|---|---|
| 7,727,249 B2 | 6/2010 | Rahmani |
| 7,731,697 B2 | 6/2010 | Porter et al. |
| 7,731,725 B2 | 6/2010 | Gadberry et al. |
| 7,736,191 B1 | 6/2010 | Sochor |
| 7,736,360 B2 | 6/2010 | Mody et al. |
| 7,736,374 B2 | 6/2010 | Vaughan et al. |
| 7,744,591 B2 | 6/2010 | Rioux et al. |
| 7,744,613 B2 | 6/2010 | Ewers et al. |
| 7,744,615 B2 | 6/2010 | Couture |
| 7,749,161 B2 | 7/2010 | Beckman et al. |
| 7,749,163 B2 | 7/2010 | Mulac et al. |
| 7,751,866 B2 | 7/2010 | Aoki et al. |
| 7,751,869 B2 | 7/2010 | Rioux et al. |
| 7,753,901 B2 | 7/2010 | Piskun et al. |
| 7,753,933 B2 | 7/2010 | Ginn et al. |
| 7,758,577 B2 | 7/2010 | Nobis et al. |
| 7,758,598 B2 | 7/2010 | Conlon et al. |
| 7,762,949 B2 | 7/2010 | Nakao |
| 7,762,959 B2 | 7/2010 | Bilsbury |
| 7,762,960 B2 | 7/2010 | Timberlake et al. |
| 7,762,998 B2 | 7/2010 | Birk et al. |
| 7,763,012 B2 | 7/2010 | Petrick et al. |
| 7,765,010 B2 | 7/2010 | Chornenky et al. |
| 7,766,819 B2 | 8/2010 | Matsumoto |
| 7,766,896 B2 | 8/2010 | Kornkven Volk et al. |
| 7,770,584 B2 | 8/2010 | Danek et al. |
| 7,771,396 B2 | 8/2010 | Stefanchik et al. |
| 7,771,416 B2 | 8/2010 | Spivey et al. |
| 7,771,437 B2 | 8/2010 | Hogg et al. |
| 7,776,035 B2 | 8/2010 | Rick et al. |
| 7,780,639 B2 | 8/2010 | Van Lue |
| 7,780,683 B2 | 8/2010 | Roue et al. |
| 7,780,691 B2 | 8/2010 | Stefanchik |
| 7,784,663 B2 | 8/2010 | Shelton, IV |
| 7,785,348 B2 | 8/2010 | Kuhns et al. |
| 7,789,825 B2 | 9/2010 | Nobis et al. |
| 7,789,827 B2 | 9/2010 | Landry |
| 7,794,409 B2 | 9/2010 | Damarati |
| 7,794,447 B2 | 9/2010 | Dann et al. |
| 7,794,458 B2 | 9/2010 | McIntyre et al. |
| 7,794,475 B2 | 9/2010 | Hess et al. |
| 7,798,386 B2 | 9/2010 | Schall et al. |
| 7,798,750 B2 | 9/2010 | Clark |
| 7,798,960 B2 | 9/2010 | Jaeger |
| 7,803,163 B2 | 9/2010 | Skakoon |
| 7,803,195 B2 | 9/2010 | Levy et al. |
| 7,813,590 B2 | 10/2010 | Horn et al. |
| 7,813,789 B2 | 10/2010 | Glukhovsky |
| 7,815,566 B2 | 10/2010 | Stefanchik et al. |
| 7,815,651 B2 | 10/2010 | Skakoon et al. |
| 7,815,652 B2 | 10/2010 | Messerly et al. |
| 7,815,659 B2 | 10/2010 | Conlon et al. |
| 7,815,662 B2 | 10/2010 | Spivey et al. |
| 7,819,836 B2 | 10/2010 | Levine et al. |
| 7,819,872 B2 | 10/2010 | Johnson et al. |
| 7,828,186 B2 | 11/2010 | Wales |
| 7,828,793 B2 | 11/2010 | Thompson et al. |
| 7,828,808 B2 | 11/2010 | Hinman et al. |
| 7,828,809 B2 | 11/2010 | Skakoon et al. |
| 7,833,156 B2 | 11/2010 | Williams et al. |
| 7,833,231 B2 | 11/2010 | Skakoon et al. |
| 7,833,238 B2 | 11/2010 | Nakao |
| 7,837,615 B2 | 11/2010 | Le et al. |
| 7,842,028 B2 | 11/2010 | Lee |
| 7,842,050 B2 | 11/2010 | Diduch et al. |
| 7,842,068 B2 | 11/2010 | Ginn |
| 7,846,087 B2 | 12/2010 | Stefanchik et al. |
| 7,846,107 B2 | 12/2010 | Hoffman et al. |
| 7,846,171 B2 | 12/2010 | Kullas et al. |
| 7,850,660 B2 | 12/2010 | Uth et al. |
| 7,850,686 B2 | 12/2010 | Nobis et al. |
| 7,850,712 B2 | 12/2010 | Conlon et al. |
| 7,857,183 B2 | 12/2010 | Shelton, IV |
| 7,857,820 B2 | 12/2010 | Skakoon et al. |
| 7,862,546 B2 | 1/2011 | Conlon et al. |
| 7,862,553 B2 | 1/2011 | Ewaschuk |
| 7,862,572 B2 | 1/2011 | Meade et al. |
| 7,862,582 B2 | 1/2011 | Ortiz et al. |
| 7,867,216 B2 | 1/2011 | Wahr et al. |
| 7,871,371 B2 | 1/2011 | Komiya et al. |
| 7,875,042 B2 | 1/2011 | Martin et al. |
| 7,879,004 B2 | 2/2011 | Seibel et al. |
| 7,883,458 B2 | 2/2011 | Hamel |
| 7,887,530 B2 | 2/2011 | Zemlok et al. |
| 7,887,550 B2 | 2/2011 | Daglow et al. |
| 7,887,558 B2 | 2/2011 | Lin et al. |
| 7,892,200 B2 | 2/2011 | Birk et al. |
| 7,892,220 B2 | 2/2011 | Faller et al. |
| 7,896,804 B2 | 3/2011 | Uchimura et al. |
| 7,896,887 B2 | 3/2011 | Rimbaugh et al. |
| 7,905,828 B2 | 3/2011 | Brock et al. |
| 7,905,830 B2 | 3/2011 | Stefanchik et al. |
| 7,909,809 B2 | 3/2011 | Scopton et al. |
| 7,914,513 B2 | 3/2011 | Voorhees, Jr. |
| 7,916,809 B2 | 3/2011 | Tsushima |
| 7,918,783 B2 | 4/2011 | Maseda et al. |
| 7,918,785 B2 | 4/2011 | Okada et al. |
| 7,918,844 B2 | 4/2011 | Byrum et al. |
| 7,918,845 B2 | 4/2011 | Saadat et al. |
| 7,918,848 B2 | 4/2011 | Lau et al. |
| 7,918,869 B2 | 4/2011 | Saadat et al. |
| 7,922,650 B2 | 4/2011 | McWeeney et al. |
| 7,922,717 B2 | 4/2011 | Sugita |
| 7,922,739 B2 | 4/2011 | Downey |
| 7,922,743 B2 | 4/2011 | Heinrich et al. |
| 7,927,271 B2 | 4/2011 | Dimitriou et al. |
| 7,931,624 B2 | 4/2011 | Smith et al. |
| 7,931,661 B2 | 4/2011 | Saadat et al. |
| 7,935,130 B2 | 5/2011 | Williams |
| 7,937,143 B2 | 5/2011 | Demarais et al. |
| 7,945,332 B2 | 5/2011 | Schechter |
| 7,947,000 B2 | 5/2011 | Vargas et al. |
| 7,951,073 B2 | 5/2011 | Freed |
| 7,953,326 B2 | 5/2011 | Farr et al. |
| 7,955,298 B2 | 6/2011 | Carroll et al. |
| 7,955,340 B2 | 6/2011 | Michlitsch et al. |
| 7,955,355 B2 | 6/2011 | Chin |
| 7,959,627 B2 | 6/2011 | Utley et al. |
| 7,959,629 B2 | 6/2011 | Young et al. |
| 7,959,642 B2 | 6/2011 | Nobis et al. |
| 7,963,192 B2 | 6/2011 | Mayenberger et al. |
| 7,963,912 B2 | 6/2011 | Zwolinski et al. |
| 7,963,975 B2 | 6/2011 | Criscuolo |
| 7,965,180 B2 | 6/2011 | Koyama |
| 7,967,808 B2 | 6/2011 | Fitzgerald et al. |
| 7,967,842 B2 | 6/2011 | Bakos |
| 7,969,473 B2 | 6/2011 | Kotoda |
| 7,972,330 B2 | 7/2011 | Alejandro et al. |
| 7,972,333 B2 | 7/2011 | Nishimura |
| 7,976,458 B2 | 7/2011 | Stefanchik et al. |
| 7,976,552 B2 | 7/2011 | Suzuki |
| 7,985,239 B2 | 7/2011 | Suzuki |
| 7,985,830 B2 | 7/2011 | Mance et al. |
| 7,988,618 B2 | 8/2011 | Mikkaichi et al. |
| 7,988,685 B2 | 8/2011 | Ziaie et al. |
| 7,988,690 B2 | 8/2011 | Chanduszko et al. |
| 7,998,132 B2 | 8/2011 | Gregorich et al. |
| 8,007,474 B2 | 8/2011 | Uth et al. |
| 8,007,495 B2 | 8/2011 | McDaniel et al. |
| 8,021,340 B2 | 9/2011 | Porter et al. |
| 8,021,358 B2 | 9/2011 | Doyle et al. |
| 8,021,362 B2 | 9/2011 | Deem et al. |
| 8,021,378 B2 | 9/2011 | Sixto, Jr. et al. |
| 8,027,710 B1 * | 9/2011 | Dannan ............ A61B 1/00009 600/407 |
| 8,029,504 B2 | 10/2011 | Long |
| 8,034,046 B2 | 10/2011 | Eidenschink |
| 8,037,591 B2 | 10/2011 | Spivey et al. |
| 8,038,596 B2 | 10/2011 | Miyake et al. |
| 8,038,612 B2 | 10/2011 | Paz |
| 8,043,289 B2 | 10/2011 | Behl et al. |
| 8,048,060 B2 | 11/2011 | Griffin et al. |
| 8,048,067 B2 | 11/2011 | Davalos et al. |
| 8,048,108 B2 | 11/2011 | Sibbitt, Jr. et al. |

(56) References Cited

U.S. PATENT DOCUMENTS

| | | |
|---|---|---|
| 8,052,597 B2 | 11/2011 | Boulais |
| 8,052,699 B1 | 11/2011 | Sherwinter |
| 8,057,462 B2 | 11/2011 | Weitzner et al. |
| 8,057,510 B2 | 11/2011 | Ginn et al. |
| 8,062,306 B2 | 11/2011 | Nobis et al. |
| 8,062,311 B2 | 11/2011 | Litscher et al. |
| 8,066,632 B2 | 11/2011 | Dario et al. |
| 8,066,702 B2 | 11/2011 | Rittman, III et al. |
| 8,070,743 B2 | 12/2011 | Kagan et al. |
| 8,070,759 B2 | 12/2011 | Stefanchik et al. |
| 8,070,804 B2 | 12/2011 | Hyde et al. |
| 8,075,478 B2 | 12/2011 | Campos |
| 8,075,567 B2 | 12/2011 | Taylor et al. |
| 8,075,572 B2 | 12/2011 | Stefanchik et al. |
| 8,075,573 B2 | 12/2011 | Gambale et al. |
| 8,075,587 B2 | 12/2011 | Ginn |
| 8,083,787 B2 | 12/2011 | Korb et al. |
| 8,088,062 B2 | 1/2012 | Zwolinski |
| 8,092,374 B2 | 1/2012 | Smith et al. |
| 8,092,549 B2 | 1/2012 | Hillis et al. |
| 8,096,459 B2 | 1/2012 | Ortiz et al. |
| 8,096,941 B2 | 1/2012 | Fowler et al. |
| 8,096,998 B2 | 1/2012 | Cresina |
| 8,097,001 B2 | 1/2012 | Nakao |
| 8,100,922 B2 | 1/2012 | Griffith |
| 8,105,342 B2 | 1/2012 | Onuki et al. |
| 8,109,872 B2 | 2/2012 | Kennedy, II et al. |
| 8,109,919 B2 | 2/2012 | Kraft et al. |
| 8,109,926 B2 | 2/2012 | Azure |
| 8,114,072 B2 | 2/2012 | Long et al. |
| 8,114,113 B2 | 2/2012 | Becker |
| 8,114,119 B2 | 2/2012 | Spivey et al. |
| 8,115,447 B2 | 2/2012 | Toya et al. |
| 8,118,738 B2 | 2/2012 | Larkin |
| 8,118,821 B2 | 2/2012 | Mouw |
| 8,118,834 B1 | 2/2012 | Goraltchouk et al. |
| 8,118,835 B2 | 2/2012 | Weisel et al. |
| 8,123,677 B2 | 2/2012 | Fujimori |
| 8,131,371 B2 | 3/2012 | Demarais et al. |
| 8,147,424 B2 | 4/2012 | Kassab et al. |
| 8,157,813 B2 | 4/2012 | Ko et al. |
| 8,157,817 B2 | 4/2012 | Bonadio et al. |
| 8,157,834 B2 | 4/2012 | Conlon |
| 8,159,549 B2 | 4/2012 | Glukhovsky et al. |
| 8,166,615 B2 | 5/2012 | Coldiron |
| 8,167,894 B2 | 5/2012 | Miles et al. |
| 8,172,772 B2 | 5/2012 | Zwolinski et al. |
| 8,172,839 B2 | 5/2012 | Kato |
| 8,182,414 B2 | 5/2012 | Handa et al. |
| 8,187,166 B2 | 5/2012 | Kuth et al. |
| 8,200,334 B1 | 6/2012 | Min et al. |
| 8,202,265 B2 | 6/2012 | Boulais |
| 8,202,295 B2 | 6/2012 | Kaplan |
| 8,206,295 B2 | 6/2012 | Kaul |
| 8,211,119 B2 | 7/2012 | Palmer et al. |
| 8,211,125 B2 | 7/2012 | Spivey |
| 8,216,224 B2 | 7/2012 | Morris et al. |
| 8,216,252 B2 | 7/2012 | Vaughan et al. |
| 8,216,255 B2 | 7/2012 | Smith et al. |
| 8,221,310 B2 | 7/2012 | Saadat et al. |
| 8,221,411 B2 | 7/2012 | Francischelli et al. |
| 8,222,385 B2 | 7/2012 | Yoshizaki et al. |
| 8,241,204 B2 | 8/2012 | Spivey |
| 8,241,309 B2 | 8/2012 | Miles et al. |
| 8,246,633 B2 | 8/2012 | Omori |
| 8,251,068 B2 | 8/2012 | Schnell |
| 8,252,057 B2 | 8/2012 | Fox |
| 8,262,563 B2 | 9/2012 | Bakos et al. |
| 8,262,655 B2 | 9/2012 | Ghabrlal et al. |
| 8,262,674 B2 | 9/2012 | Daglow et al. |
| 8,262,680 B2 | 9/2012 | Swain et al. |
| 8,267,854 B2 | 9/2012 | Asada et al. |
| 8,269,823 B2 | 9/2012 | Hirakawa et al. |
| 8,277,373 B2 | 10/2012 | Maahs et al. |
| 8,282,665 B2 | 10/2012 | Kieturakis et al. |
| 8,298,161 B2 | 10/2012 | Vargas |
| 8,303,485 B2 | 11/2012 | Segawa et al. |
| 8,303,581 B2 | 11/2012 | Arts et al. |
| 8,308,682 B2 | 11/2012 | Kramer et al. |
| 8,308,738 B2 | 11/2012 | Nobis et al. |
| 8,308,743 B2 | 11/2012 | Matsuno et al. |
| 8,313,496 B2 | 11/2012 | Sauer et al. |
| 8,315,714 B2 | 11/2012 | Daglow et al. |
| 8,317,806 B2 | 11/2012 | Coe et al. |
| 8,328,836 B2 | 12/2012 | Conlon et al. |
| 8,333,691 B2 | 12/2012 | Schaaf |
| 8,333,777 B2 | 12/2012 | Schaller et al. |
| 8,337,394 B2 | 12/2012 | Vakharia |
| 8,337,492 B2 | 12/2012 | Kunis et al. |
| 8,337,510 B2 | 12/2012 | Rieber et al. |
| 8,343,041 B2 | 1/2013 | Byers et al. |
| 8,348,827 B2 | 1/2013 | Zwolinski |
| 8,353,487 B2 | 1/2013 | Trusty et al. |
| 8,357,170 B2 | 1/2013 | Stefanchik |
| 8,359,093 B2 | 1/2013 | Wariar |
| 8,361,066 B2 | 1/2013 | Long et al. |
| 8,361,112 B2 | 1/2013 | Carroll, II et al. |
| 8,366,606 B2 | 2/2013 | Watanabe et al. |
| 8,366,733 B2 | 2/2013 | Gabel et al. |
| 8,377,044 B2 | 2/2013 | Coe et al. |
| 8,377,057 B2 | 2/2013 | Rick et al. |
| 8,382,790 B2 | 2/2013 | Uenohara et al. |
| 8,388,653 B2 | 3/2013 | Nobis et al. |
| 8,394,090 B2 | 3/2013 | Ootsubo |
| 8,397,335 B2 | 3/2013 | Gordin et al. |
| 8,403,926 B2 | 3/2013 | Nobis et al. |
| 8,409,076 B2 | 4/2013 | Pang et al. |
| 8,409,197 B2 | 4/2013 | Slater |
| 8,409,200 B2 | 4/2013 | Holcomb et al. |
| 8,425,505 B2 | 4/2013 | Long |
| 8,430,811 B2 | 4/2013 | Hess et al. |
| 8,449,452 B2 | 5/2013 | Iddan et al. |
| 8,449,538 B2 | 5/2013 | Long |
| 8,454,594 B2 | 6/2013 | Demarais et al. |
| 8,460,275 B2 | 6/2013 | Taylor et al. |
| 8,465,419 B2 | 6/2013 | Moriyama |
| 8,465,484 B2 | 6/2013 | Davalos et al. |
| 8,469,993 B2 | 6/2013 | Rothberg et al. |
| 8,475,359 B2 | 7/2013 | Asada et al. |
| 8,475,361 B2 | 7/2013 | Barlow et al. |
| 8,475,452 B2 | 7/2013 | Van Wyk et al. |
| 8,480,657 B2 | 7/2013 | Bakos |
| 8,480,689 B2 | 7/2013 | Spivey et al. |
| 8,485,968 B2 | 7/2013 | Weimer et al. |
| 8,496,574 B2 | 7/2013 | Trusty et al. |
| 8,500,697 B2 | 8/2013 | Kurth et al. |
| 8,506,564 B2 | 8/2013 | Long et al. |
| 8,512,335 B2 | 8/2013 | Cheng et al. |
| 8,517,921 B2 | 8/2013 | Tremaglio et al. |
| 8,518,024 B2 | 8/2013 | Williams et al. |
| 8,518,052 B2 | 8/2013 | Burgermeister et al. |
| 8,518,062 B2 | 8/2013 | Cole et al. |
| 8,523,884 B2 | 9/2013 | Stam et al. |
| 8,523,939 B1 | 9/2013 | Hausen |
| 8,529,563 B2 | 9/2013 | Long et al. |
| 8,540,744 B2 | 9/2013 | Spivey et al. |
| 8,545,396 B2 | 10/2013 | Cover et al. |
| 8,545,450 B2 | 10/2013 | Voegele et al. |
| 8,551,058 B2 | 10/2013 | Measamer et al. |
| 8,562,513 B2 | 10/2013 | Yamatani |
| 8,562,602 B2 | 10/2013 | Azure |
| 8,568,410 B2 | 10/2013 | Vakharia et al. |
| 8,579,176 B2 | 11/2013 | Smith et al. |
| 8,579,897 B2 | 11/2013 | Vakharia et al. |
| 8,585,644 B2 | 11/2013 | Rodriguez Lelis et al. |
| 8,602,970 B2 | 12/2013 | Muyari et al. |
| 8,603,138 B2 | 12/2013 | Faller et al. |
| 8,608,652 B2 | 12/2013 | Voegele et al. |
| 8,617,156 B2 | 12/2013 | Werneth et al. |
| 8,628,522 B2 * | 1/2014 | Ibrahim ............ A61B 18/1492 606/32 |
| 8,632,534 B2 | 1/2014 | Pearson et al. |
| 8,632,563 B2 | 1/2014 | Nagase et al. |
| 8,636,648 B2 | 1/2014 | Gazdzinskl |

(56) References Cited

U.S. PATENT DOCUMENTS

| | | |
|---|---|---|
| 8,636,650 B2 | 1/2014 | Lee |
| 8,636,730 B2 | 1/2014 | Keppel |
| 8,640,940 B2 | 2/2014 | Ohdaira |
| 8,641,728 B2 | 2/2014 | Stokes et al. |
| 8,652,150 B2 | 2/2014 | Swain et al. |
| 8,657,174 B2 | 2/2014 | Yates et al. |
| 8,663,236 B2 | 3/2014 | Chen et al. |
| 8,663,263 B2 | 3/2014 | Smith |
| 8,668,686 B2 | 3/2014 | Govari et al. |
| 8,678,999 B2 | 3/2014 | Isaacson |
| 8,679,003 B2 | 3/2014 | Spivey |
| 8,684,967 B2 | 4/2014 | Engel et al. |
| 8,685,058 B2 | 4/2014 | Wilk |
| 8,702,753 B2 | 4/2014 | Mikkaichi et al. |
| 8,704,923 B2 | 4/2014 | Ogasawara et al. |
| 8,715,281 B2 | 5/2014 | Barlow et al. |
| 8,721,658 B2 | 5/2014 | Kahle et al. |
| 8,723,936 B2 | 5/2014 | Amling et al. |
| 8,727,967 B2 | 5/2014 | Weitzner |
| 8,738,141 B2 | 5/2014 | Smith et al. |
| 8,747,401 B2 | 6/2014 | Gonzalez et al. |
| 8,753,262 B2 | 6/2014 | Sugiyama et al. |
| 8,753,335 B2 | 6/2014 | Moshe et al. |
| 8,764,735 B2 | 7/2014 | Coe et al. |
| 8,771,173 B2 | 7/2014 | Fonger et al. |
| 8,771,260 B2 | 7/2014 | Conlon et al. |
| 8,774,913 B2 | 7/2014 | Demarais et al. |
| 8,784,403 B2 | 7/2014 | Cefai et al. |
| 8,784,436 B2 | 7/2014 | Ho et al. |
| 8,795,161 B2 | 8/2014 | Carter |
| 8,821,520 B2 | 9/2014 | Schwemberger et al. |
| 8,821,532 B2 | 9/2014 | Schaeffer |
| 8,828,031 B2 | 9/2014 | Fox et al. |
| 8,834,461 B2 | 9/2014 | Werneth et al. |
| 8,845,656 B2 | 9/2014 | Skakoon et al. |
| 8,876,701 B2 | 11/2014 | Surti et al. |
| 8,876,772 B2 | 11/2014 | Weber et al. |
| 8,880,185 B2 | 11/2014 | Hastings et al. |
| 8,882,786 B2 | 11/2014 | Bearinger et al. |
| 8,888,792 B2 | 11/2014 | Harris et al. |
| 8,906,035 B2 | 12/2014 | Zwolinski et al. |
| 8,911,452 B2 | 12/2014 | Skakoon et al. |
| 8,920,442 B2 | 12/2014 | Sibbitt, Jr. et al. |
| 8,926,606 B2 | 1/2015 | Davalos et al. |
| 8,932,208 B2 | 1/2015 | Kendale et al. |
| 8,939,897 B2 | 1/2015 | Nobis |
| 8,939,969 B2 | 1/2015 | Temelli et al. |
| 8,956,352 B2 | 2/2015 | Mauch et al. |
| 8,974,374 B2 | 3/2015 | Schostek et al. |
| 8,979,751 B2 | 3/2015 | George |
| 8,986,199 B2 | 3/2015 | Weisenburgh, II et al. |
| 8,986,343 B2 | 3/2015 | Bourque et al. |
| 8,992,517 B2 | 3/2015 | Davalos et al. |
| 9,005,198 B2 | 4/2015 | Long et al. |
| 9,011,431 B2 | 4/2015 | Long et al. |
| 9,028,483 B2 | 5/2015 | Long et al. |
| 9,036,015 B2 | 5/2015 | Verburgh et al. |
| 9,044,247 B2 | 6/2015 | Kato |
| 9,049,987 B2 | 6/2015 | Conlon et al. |
| 9,060,782 B2 | 6/2015 | Daniel et al. |
| 9,066,655 B2 | 6/2015 | Stefanchik et al. |
| 9,078,662 B2 | 7/2015 | Bakos et al. |
| 9,084,621 B2 | 7/2015 | Weitzner et al. |
| 9,089,323 B2 | 7/2015 | Bonutti et al. |
| 9,125,557 B2 | 9/2015 | Lien et al. |
| 9,125,631 B2 | 9/2015 | Smith et al. |
| 9,125,639 B2 | 9/2015 | Mathis et al. |
| 9,138,586 B2 | 9/2015 | Eiger |
| 9,149,172 B2 | 10/2015 | Iddan et al. |
| 9,155,587 B2 | 10/2015 | Wilis et al. |
| 9,162,050 B2 | 10/2015 | Boling |
| 9,186,203 B2 | 11/2015 | Spivey et al. |
| 9,198,733 B2 | 12/2015 | Neal, II et al. |
| 9,220,526 B2 | 12/2015 | Conlon |
| 9,226,772 B2 | 1/2016 | Fox |
| 9,233,241 B2 | 1/2016 | Long |
| 9,248,278 B2 | 2/2016 | Crosby et al. |
| 9,254,169 B2 | 2/2016 | Long et al. |
| 9,265,407 B2 | 2/2016 | Goldfarb et al. |
| 9,271,796 B2 | 3/2016 | Buysse et al. |
| 9,277,957 B2 | 3/2016 | Long et al. |
| 9,295,485 B2 | 3/2016 | Conlon et al. |
| 9,308,049 B2 | 4/2016 | Dejima |
| 9,314,620 B2 | 4/2016 | Long et al. |
| 9,339,328 B2 | 5/2016 | Ortiz et al. |
| 9,345,462 B2 | 5/2016 | Weitzner et al. |
| 9,352,152 B2 | 5/2016 | Lindenthaler et al. |
| 9,364,278 B2 | 6/2016 | DeCarlo et al. |
| 9,370,341 B2 | 6/2016 | Ceniccola et al. |
| 9,375,268 B2 | 6/2016 | Long |
| 9,427,255 B2 | 8/2016 | Griffith et al. |
| 9,486,241 B2 | 11/2016 | Zeiner et al. |
| 9,492,148 B2 | 11/2016 | Ginn et al. |
| 9,545,290 B2 | 1/2017 | Tellio et al. |
| 9,549,719 B2 | 1/2017 | Shohat et al. |
| 9,566,126 B2 | 2/2017 | Weitzner et al. |
| 9,572,623 B2 | 2/2017 | Long |
| 9,596,980 B2 | 3/2017 | Marescaux et al. |
| 9,596,994 B2 | 3/2017 | Futrell et al. |
| 9,598,691 B2 | 3/2017 | Davalos |
| 9,627,120 B2 | 4/2017 | Scott et al. |
| 9,636,251 B2 | 5/2017 | Swann |
| 9,668,725 B2 | 6/2017 | Beaven |
| 9,694,175 B2 | 7/2017 | Tyson, Jr. |
| 9,700,334 B2 | 7/2017 | Hinman et al. |
| 9,788,885 B2 | 10/2017 | Long et al. |
| 9,788,888 B2 | 10/2017 | Bakos et al. |
| 9,788,890 B2 | 10/2017 | Toth et al. |
| 9,808,597 B2 | 11/2017 | Vargas et al. |
| 9,833,282 B2 | 12/2017 | Jun |
| 9,833,595 B2 | 12/2017 | Gonzalez |
| 9,861,350 B2 | 1/2018 | Serina et al. |
| 9,867,652 B2 | 1/2018 | Sano et al. |
| 9,877,781 B2 | 1/2018 | Grasse et al. |
| 9,883,910 B2 | 2/2018 | Conlon et al. |
| 9,974,944 B2 | 5/2018 | Sudam et al. |
| 10,004,558 B2 | 6/2018 | Long et al. |
| 10,010,666 B2 | 7/2018 | Rubinsky et al. |
| 10,071,012 B2 | 9/2018 | Larson et al. |
| 10,092,291 B2 | 10/2018 | Voegele et al. |
| 10,098,527 B2 | 10/2018 | Weisenburgh, II et al. |
| 10,098,691 B2 | 10/2018 | Long et al. |
| 10,105,141 B2 | 10/2018 | Harris et al. |
| 10,206,709 B2 | 2/2019 | Griffith et al. |
| 10,208,158 B2 | 2/2019 | Banister et al. |
| 10,258,406 B2 | 4/2019 | Long |
| 10,278,761 B2 | 5/2019 | Long et al. |
| 10,300,268 B2 | 5/2019 | Skakoon et al. |
| 10,314,603 B2 | 6/2019 | Conlon |
| 10,314,649 B2 | 6/2019 | Bakos et al. |
| 10,321,927 B2 | 6/2019 | Hinman |
| 10,342,598 B2 | 7/2019 | Long et al. |
| 10,376,314 B2 | 8/2019 | van der Weide et al. |
| 10,390,715 B2 | 8/2019 | Rich et al. |
| 10,448,989 B2 | 10/2019 | Arena et al. |
| 10,478,248 B2 | 11/2019 | Long |
| 10,492,880 B2 | 12/2019 | Tellio et al. |
| 10,660,632 B2 | 5/2020 | Torrie et al. |
| 2001/0023333 A1 | 9/2001 | Wise et al. |
| 2002/0019641 A1 | 2/2002 | Truwit |
| 2002/0022857 A1 | 2/2002 | Goldsteen et al. |
| 2002/0023353 A1 | 2/2002 | Ting-Kung |
| 2002/0029055 A1 | 3/2002 | Bonutti |
| 2002/0042562 A1 | 4/2002 | Meron et al. |
| 2002/0068945 A1 | 6/2002 | Sixto et al. |
| 2002/0082551 A1 | 6/2002 | Yachia et al. |
| 2002/0095164 A1 | 7/2002 | Andreas et al. |
| 2002/0133115 A1 | 9/2002 | Gordon et al. |
| 2002/0133178 A1 | 9/2002 | Muramatsu et al. |
| 2002/0138086 A1 | 9/2002 | Sixto et al. |
| 2002/0165592 A1 | 11/2002 | Glukhovsky et al. |
| 2002/0173786 A1 | 11/2002 | Kortenbach et al. |
| 2002/0198541 A1 | 12/2002 | Smith et al. |
| 2003/0014090 A1 | 1/2003 | Abrahamson |

(56) References Cited

U.S. PATENT DOCUMENTS

| | | |
|---|---|---|
| 2003/0018373 A1 | 1/2003 | Eckhardt et al. |
| 2003/0069602 A1 | 4/2003 | Jacobs et al. |
| 2003/0078471 A1 | 4/2003 | Foley et al. |
| 2003/0083681 A1 | 5/2003 | Moutafis et al. |
| 2003/0093104 A1 | 5/2003 | Bonner et al. |
| 2003/0114731 A1 | 6/2003 | Cadeddu et al. |
| 2003/0114732 A1 | 6/2003 | Webler et al. |
| 2003/0120257 A1 | 6/2003 | Houston et al. |
| 2003/0124009 A1 | 7/2003 | Ravi et al. |
| 2003/0130656 A1 | 7/2003 | Levin |
| 2003/0139646 A1 | 7/2003 | Sharrow et al. |
| 2003/0158521 A1 | 8/2003 | Ameri |
| 2003/0167062 A1 | 9/2003 | Gambale et al. |
| 2003/0170898 A1 | 9/2003 | Gundersen et al. |
| 2003/0171650 A1* | 9/2003 | Tartaglia ............ A61B 1/00147 600/114 |
| 2003/0181900 A1 | 9/2003 | Long |
| 2003/0187351 A1 | 10/2003 | Franck et al. |
| 2003/0225312 A1 | 12/2003 | Suzuki et al. |
| 2003/0225332 A1 | 12/2003 | Okada et al. |
| 2003/0229269 A1 | 12/2003 | Humphrey |
| 2003/0229371 A1 | 12/2003 | Whitworth |
| 2004/0002683 A1 | 1/2004 | Nicholson et al. |
| 2004/0024414 A1 | 2/2004 | Downing |
| 2004/0045133 A1 | 3/2004 | Buettell |
| 2004/0054377 A1 | 3/2004 | Foster et al. |
| 2004/0092970 A1 | 5/2004 | Xavier |
| 2004/0098007 A1 | 5/2004 | Heiss |
| 2004/0101456 A1 | 5/2004 | Kuroshima et al. |
| 2004/0104999 A1 | 6/2004 | Okada |
| 2004/0133089 A1 | 7/2004 | Kilcoyne et al. |
| 2004/0136779 A1 | 7/2004 | Bhaskar |
| 2004/0138529 A1 | 7/2004 | Witshire et al. |
| 2004/0138587 A1 | 7/2004 | Lyons |
| 2004/0138747 A1 | 7/2004 | Kaladelfos |
| 2004/0161451 A1 | 8/2004 | Pierce et al. |
| 2004/0167545 A1 | 8/2004 | Sadler et al. |
| 2004/0176699 A1 | 9/2004 | Walker et al. |
| 2004/0186350 A1 | 9/2004 | Brenneman et al. |
| 2004/0193009 A1 | 9/2004 | Jaffe et al. |
| 2004/0193186 A1 | 9/2004 | Kortenbach et al. |
| 2004/0193188 A1 | 9/2004 | Francese |
| 2004/0193189 A1 | 9/2004 | Kortenbach et al. |
| 2004/0193200 A1 | 9/2004 | Dworschak et al. |
| 2004/0199052 A1 | 10/2004 | Banik et al. |
| 2004/0199159 A1 | 10/2004 | Lee et al. |
| 2004/0206859 A1 | 10/2004 | Chong et al. |
| 2004/0210245 A1 | 10/2004 | Erickson et al. |
| 2004/0225186 A1 | 11/2004 | Horne et al. |
| 2004/0230097 A1* | 11/2004 | Stefanchik ......... A61B 1/00073 600/127 |
| 2004/0243108 A1 | 12/2004 | Suzuki |
| 2004/0249367 A1 | 12/2004 | Saadat et al. |
| 2004/0249394 A1 | 12/2004 | Morris et al. |
| 2004/0249443 A1 | 12/2004 | Shanley et al. |
| 2004/0254572 A1 | 12/2004 | McIntyre et al. |
| 2004/0260315 A1 | 12/2004 | Dell et al. |
| 2004/0260337 A1 | 12/2004 | Freed |
| 2005/0000553 A1 | 1/2005 | Noguchi et al. |
| 2005/0004515 A1 | 1/2005 | Hart et al. |
| 2005/0010211 A1 | 1/2005 | Suzuki |
| 2005/0015103 A1 | 1/2005 | Popov |
| 2005/0043690 A1 | 2/2005 | Todd |
| 2005/0059963 A1 | 3/2005 | Phan et al. |
| 2005/0059964 A1 | 3/2005 | Fitz |
| 2005/0065509 A1 | 3/2005 | Coldwell et al. |
| 2005/0070947 A1 | 3/2005 | Franer et al. |
| 2005/0080435 A1 | 4/2005 | Smith et al. |
| 2005/0085693 A1 | 4/2005 | Belson et al. |
| 2005/0085832 A1 | 4/2005 | Sancoff et al. |
| 2005/0090837 A1 | 4/2005 | Sixto et al. |
| 2005/0096502 A1 | 5/2005 | Khalili |
| 2005/0101837 A1 | 5/2005 | Kalloo et al. |
| 2005/0101838 A1 | 5/2005 | Camillocci et al. |
| 2005/0107663 A1 | 5/2005 | Saadat et al. |
| 2005/0107664 A1 | 5/2005 | Kalloo et al. |
| 2005/0119613 A1 | 6/2005 | Moenning et al. |
| 2005/0124855 A1 | 6/2005 | Jaffe et al. |
| 2005/0125010 A1 | 6/2005 | Smith et al. |
| 2005/0131457 A1 | 6/2005 | Douglas et al. |
| 2005/0137454 A1 | 6/2005 | Saadat et al. |
| 2005/0143690 A1 | 6/2005 | High |
| 2005/0143774 A1 | 6/2005 | Polo |
| 2005/0143803 A1 | 6/2005 | Watson et al. |
| 2005/0149087 A1 | 7/2005 | Ahlberg et al. |
| 2005/0149096 A1 | 7/2005 | Hilal et al. |
| 2005/0165272 A1 | 7/2005 | Okada et al. |
| 2005/0165378 A1 | 7/2005 | Heinrich et al. |
| 2005/0165411 A1 | 7/2005 | Orban |
| 2005/0165429 A1 | 7/2005 | Douglas et al. |
| 2005/0182429 A1 | 8/2005 | Yamanouchi |
| 2005/0192478 A1 | 9/2005 | Williams et al. |
| 2005/0192602 A1 | 9/2005 | Manzo |
| 2005/0209624 A1 | 9/2005 | Vijay |
| 2005/0215858 A1 | 9/2005 | Vail |
| 2005/0216036 A1 | 9/2005 | Nakao |
| 2005/0222495 A1 | 10/2005 | Okada et al. |
| 2005/0228224 A1 | 10/2005 | Okada et al. |
| 2005/0228406 A1 | 10/2005 | Bose |
| 2005/0234297 A1* | 10/2005 | Devierre ............ A61B 1/00087 600/153 |
| 2005/0240249 A1 | 10/2005 | Tu et al. |
| 2005/0250987 A1 | 11/2005 | Ewers et al. |
| 2005/0251176 A1 | 11/2005 | Swanstrom et al. |
| 2005/0256524 A1 | 11/2005 | Long et al. |
| 2005/0261711 A1 | 11/2005 | Okada et al. |
| 2005/0267492 A1 | 12/2005 | Poncet et al. |
| 2005/0272977 A1 | 12/2005 | Saadat et al. |
| 2005/0274935 A1 | 12/2005 | Nelson |
| 2005/0277956 A1 | 12/2005 | Francese et al. |
| 2005/0288550 A1* | 12/2005 | Mathis ................ A61B 1/0014 600/104 |
| 2005/0288555 A1 | 12/2005 | Binmoeller |
| 2006/0004406 A1 | 1/2006 | Wehrstein et al. |
| 2006/0004409 A1 | 1/2006 | Nobis et al. |
| 2006/0004410 A1 | 1/2006 | Nobis et al. |
| 2006/0015009 A1 | 1/2006 | Jaffe et al. |
| 2006/0015131 A1 | 1/2006 | Kierce et al. |
| 2006/0020167 A1 | 1/2006 | Sitzmann |
| 2006/0025654 A1 | 2/2006 | Suzuki et al. |
| 2006/0025781 A1 | 2/2006 | Young et al. |
| 2006/0025812 A1 | 2/2006 | Shelton |
| 2006/0036267 A1 | 2/2006 | Saadat et al. |
| 2006/0041188 A1 | 2/2006 | Dirusso et al. |
| 2006/0058582 A1 | 3/2006 | Maahs et al. |
| 2006/0064083 A1 | 3/2006 | Khalaj et al. |
| 2006/0069304 A1* | 3/2006 | Takemoto ......... A61B 1/00087 600/104 |
| 2006/0069424 A1 | 3/2006 | Acosta et al. |
| 2006/0069429 A1 | 3/2006 | Spence et al. |
| 2006/0074413 A1 | 4/2006 | Behzadian |
| 2006/0089528 A1 | 4/2006 | Tartaglia et al. |
| 2006/0095031 A1 | 5/2006 | Ormsby |
| 2006/0100687 A1 | 5/2006 | Fahey et al. |
| 2006/0111703 A1 | 5/2006 | Kunis et al. |
| 2006/0111704 A1 | 5/2006 | Brenneman et al. |
| 2006/0129166 A1 | 6/2006 | Lavelle |
| 2006/0135962 A1 | 6/2006 | Kick et al. |
| 2006/0135971 A1 | 6/2006 | Swanstrom et al. |
| 2006/0142652 A1 | 6/2006 | Keenan |
| 2006/0142790 A1 | 6/2006 | Gertner |
| 2006/0142798 A1 | 6/2006 | Holman et al. |
| 2006/0149129 A1 | 7/2006 | Watts et al. |
| 2006/0149131 A1 | 7/2006 | Or |
| 2006/0149132 A1 | 7/2006 | Iddan |
| 2006/0161190 A1 | 7/2006 | Gadberry et al. |
| 2006/0167482 A1 | 7/2006 | Swain et al. |
| 2006/0173452 A1 | 8/2006 | Buysse et al. |
| 2006/0178560 A1 | 8/2006 | Saadat et al. |
| 2006/0183975 A1 | 8/2006 | Saadat et al. |
| 2006/0184161 A1 | 8/2006 | Maahs et al. |
| 2006/0189844 A1 | 8/2006 | Tien |
| 2006/0200005 A1 | 9/2006 | Bjork et al. |
| 2006/0200121 A1 | 9/2006 | Mowery |

(56) References Cited

U.S. PATENT DOCUMENTS

| | | |
|---|---|---|
| 2006/0200169 A1 | 9/2006 | Sniffin |
| 2006/0200170 A1 | 9/2006 | Aranyi |
| 2006/0217665 A1 | 9/2006 | Prosek |
| 2006/0217742 A1 | 9/2006 | Messerly et al. |
| 2006/0237023 A1 | 10/2006 | Cox et al. |
| 2006/0241570 A1 | 10/2006 | Wilk |
| 2006/0241691 A1 | 10/2006 | Wilk |
| 2006/0247500 A1 | 11/2006 | Voegele et al. |
| 2006/0247576 A1 | 11/2006 | Poncet |
| 2006/0247663 A1 | 11/2006 | Schwartz et al. |
| 2006/0253004 A1 | 11/2006 | Frisch et al. |
| 2006/0259010 A1 | 11/2006 | Stefanchik et al. |
| 2006/0259073 A1 | 11/2006 | Miyamoto et al. |
| 2006/0264752 A1 | 11/2006 | Rubinsky et al. |
| 2006/0264904 A1 | 11/2006 | Kerby et al. |
| 2006/0270902 A1 | 11/2006 | Igarashi et al. |
| 2006/0271042 A1 | 11/2006 | Latterell et al. |
| 2006/0271102 A1 | 11/2006 | Bosshard et al. |
| 2006/0276835 A1 | 12/2006 | Uchida |
| 2006/0287644 A1 | 12/2006 | Inganas et al. |
| 2006/0287666 A1 | 12/2006 | Saadat et al. |
| 2007/0000550 A1 | 1/2007 | Osinski |
| 2007/0005019 A1 | 1/2007 | Okishige |
| 2007/0015965 A1 | 1/2007 | Cox et al. |
| 2007/0032701 A1 | 2/2007 | Fowler et al. |
| 2007/0051375 A1 | 3/2007 | Milliman |
| 2007/0066869 A1 | 3/2007 | Hoffman |
| 2007/0067017 A1 | 3/2007 | Trapp |
| 2007/0073102 A1 | 3/2007 | Matsuno et al. |
| 2007/0078439 A1 | 4/2007 | Grandt et al. |
| 2007/0083192 A1 | 4/2007 | Welch |
| 2007/0100375 A1 | 5/2007 | Mikkaichi et al. |
| 2007/0100376 A1 | 5/2007 | Mikkaichi et al. |
| 2007/0106113 A1 | 5/2007 | Ravo |
| 2007/0106317 A1 | 5/2007 | Shelton et al. |
| 2007/0112251 A1 | 5/2007 | Nakhuda |
| 2007/0112342 A1 | 5/2007 | Pearson et al. |
| 2007/0112385 A1 | 5/2007 | Conlon |
| 2007/0112417 A1 | 5/2007 | Shanley et al. |
| 2007/0118115 A1 | 5/2007 | Artale et al. |
| 2007/0123840 A1 | 5/2007 | Cox |
| 2007/0135803 A1 | 6/2007 | Belson |
| 2007/0142706 A1 | 6/2007 | Matsui et al. |
| 2007/0142710 A1 | 6/2007 | Yokoi et al. |
| 2007/0142779 A1 | 6/2007 | Duane et al. |
| 2007/0156028 A1 | 7/2007 | Van Lue et al. |
| 2007/0161855 A1 | 7/2007 | Mikkaichi et al. |
| 2007/0167901 A1 | 7/2007 | Herrig et al. |
| 2007/0173686 A1 | 7/2007 | Lin et al. |
| 2007/0173691 A1 | 7/2007 | Yokoi et al. |
| 2007/0173869 A1 | 7/2007 | Gannoe et al. |
| 2007/0173870 A2 | 7/2007 | Zacharias |
| 2007/0173872 A1 | 7/2007 | Neuenfeldt |
| 2007/0179525 A1 | 8/2007 | Frecker et al. |
| 2007/0191904 A1 | 8/2007 | Libbus et al. |
| 2007/0198057 A1 | 8/2007 | Gelbart et al. |
| 2007/0203398 A1 | 8/2007 | Bonadio et al. |
| 2007/0208336 A1 | 9/2007 | Kim et al. |
| 2007/0208407 A1 | 9/2007 | Gerdts et al. |
| 2007/0213754 A1 | 9/2007 | Mikkaichi et al. |
| 2007/0225552 A1 | 9/2007 | Segawa et al. |
| 2007/0233040 A1 | 10/2007 | Macnamara et al. |
| 2007/0244356 A1 | 10/2007 | Carrillo et al. |
| 2007/0244358 A1 | 10/2007 | Lee |
| 2007/0255303 A1 | 11/2007 | Bakos et al. |
| 2007/0260121 A1 | 11/2007 | Bakos et al. |
| 2007/0260242 A1 | 11/2007 | Dycus et al. |
| 2007/0260273 A1 | 11/2007 | Cropper et al. |
| 2007/0260302 A1 | 11/2007 | Igaki |
| 2007/0265494 A1 | 11/2007 | Leanna et al. |
| 2007/0270629 A1 | 11/2007 | Charles |
| 2007/0270907 A1 | 11/2007 | Stokes et al. |
| 2007/0282165 A1 | 12/2007 | Hopkins et al. |
| 2008/0004650 A1 | 1/2008 | George |
| 2008/0004656 A1 | 1/2008 | Livneh |
| 2008/0015413 A1 | 1/2008 | Barlow et al. |
| 2008/0021416 A1 | 1/2008 | Aral et al. |
| 2008/0022927 A1 | 1/2008 | Zhang et al. |
| 2008/0027387 A1 | 1/2008 | Grabinsky |
| 2008/0033244 A1 | 2/2008 | Matsui et al. |
| 2008/0058586 A1 | 3/2008 | Karpiel |
| 2008/0065169 A1 | 3/2008 | Colliou et al. |
| 2008/0082108 A1 | 4/2008 | Skakoon et al. |
| 2008/0091068 A1 | 4/2008 | Terliuc |
| 2008/0097159 A1 | 4/2008 | Ishiguro |
| 2008/0097472 A1 | 4/2008 | Agmon et al. |
| 2008/0103527 A1 | 5/2008 | Martin et al. |
| 2008/0114384 A1 | 5/2008 | Chang et al. |
| 2008/0125765 A1 | 5/2008 | Berenshteyn et al. |
| 2008/0125774 A1 | 5/2008 | Palanker et al. |
| 2008/0125796 A1 | 5/2008 | Graham |
| 2008/0140069 A1 | 6/2008 | Filloux et al. |
| 2008/0140071 A1 | 6/2008 | Vegesna |
| 2008/0150754 A1 | 6/2008 | Quendt |
| 2008/0171907 A1 | 7/2008 | Long et al. |
| 2008/0177141 A1* | 7/2008 | Wu .................... A61B 1/00147 600/112 |
| 2008/0188710 A1 | 8/2008 | Segawa et al. |
| 2008/0200755 A1 | 8/2008 | Bakos |
| 2008/0200762 A1 | 8/2008 | Stokes et al. |
| 2008/0200911 A1 | 8/2008 | Long |
| 2008/0200933 A1 | 8/2008 | Bakos et al. |
| 2008/0200934 A1 | 8/2008 | Fox |
| 2008/0208213 A1 | 8/2008 | Benjamin et al. |
| 2008/0214890 A1 | 9/2008 | Motai et al. |
| 2008/0215070 A1 | 9/2008 | Gildenberg |
| 2008/0221587 A1 | 9/2008 | Schwartz |
| 2008/0228213 A1 | 9/2008 | Blakeney et al. |
| 2008/0230972 A1 | 9/2008 | Ganley |
| 2008/0243148 A1 | 10/2008 | Mikkaichi et al. |
| 2008/0255647 A1 | 10/2008 | Jensen et al. |
| 2008/0262513 A1 | 10/2008 | Stabler et al. |
| 2008/0262524 A1 | 10/2008 | Bangera et al. |
| 2008/0262540 A1 | 10/2008 | Bangera et al. |
| 2008/0287801 A1 | 11/2008 | Magnln et al. |
| 2008/0294154 A1* | 11/2008 | Ibrahim ............. A61B 18/1492 601/3 |
| 2008/0294159 A1 | 11/2008 | Akahoshi et al. |
| 2008/1275474 | 11/2008 | Martin et al. |
| 2008/0300458 A1 | 12/2008 | Kim et al. |
| 2008/0300461 A1 | 12/2008 | Shaw et al. |
| 2008/0300571 A1 | 12/2008 | LePivert |
| 2008/0306493 A1 | 12/2008 | Shibata et al. |
| 2008/0309758 A1 | 12/2008 | Karasawa et al. |
| 2008/0312502 A1 | 12/2008 | Swain et al. |
| 2009/0018396 A1 | 1/2009 | Takizawa et al. |
| 2009/0030278 A1 | 1/2009 | Minakuchi |
| 2009/0048486 A1 | 2/2009 | Surti |
| 2009/0054728 A1 | 2/2009 | Trusty |
| 2009/0062788 A1 | 3/2009 | Long et al. |
| 2009/0062795 A1 | 3/2009 | Vakharia et al. |
| 2009/0069786 A1 | 3/2009 | Vesely et al. |
| 2009/0076536 A1* | 3/2009 | Rentschler ......... A61B 17/3468 606/192 |
| 2009/0078736 A1 | 3/2009 | Van Lue |
| 2009/0082627 A1 | 3/2009 | Karasawa et al. |
| 2009/0093690 A1 | 4/2009 | Yoshizawa |
| 2009/0099414 A1 | 4/2009 | Goto et al. |
| 2009/0112059 A1 | 4/2009 | Nobis |
| 2009/0112063 A1 | 4/2009 | Bakos et al. |
| 2009/0131751 A1 | 5/2009 | Spivey et al. |
| 2009/0143639 A1 | 6/2009 | Stark |
| 2009/0143649 A1 | 6/2009 | Rossi |
| 2009/0143794 A1 | 6/2009 | Conlon et al. |
| 2009/0171373 A1* | 7/2009 | Farritor ................ A61B 90/37 606/130 |
| 2009/0177219 A1 | 7/2009 | Conlon |
| 2009/0182332 A1 | 7/2009 | Long et al. |
| 2009/0187073 A1* | 7/2009 | Karasawa ............ A61B 1/041 600/114 |
| 2009/0192344 A1 | 7/2009 | Bakos et al. |
| 2009/0192534 A1 | 7/2009 | Ortiz et al. |
| 2009/0198212 A1 | 8/2009 | Timberlake et al. |
| 2009/0198231 A1 | 8/2009 | Esser et al. |

(56) References Cited

U.S. PATENT DOCUMENTS

| | | |
|---|---|---|
| 2009/0198251 A1 | 8/2009 | Ransbury et al. |
| 2009/0209804 A1 | 8/2009 | Seiler et al. |
| 2009/0210000 A1 | 8/2009 | Sullivan et al. |
| 2009/0221873 A1 | 9/2009 | McGrath |
| 2009/0228001 A1 | 9/2009 | Pacey |
| 2009/0234278 A1 | 9/2009 | Eck |
| 2009/0254019 A1 | 10/2009 | Gehl et al. |
| 2009/0259105 A1 | 10/2009 | Miyano et al. |
| 2009/0281559 A1 | 11/2009 | Swain et al. |
| 2009/0287045 A1 | 11/2009 | Mitelberg et al. |
| 2009/0287236 A1 | 11/2009 | Bakos et al. |
| 2009/0292167 A1 | 11/2009 | Kimoto |
| 2009/0306470 A1 | 12/2009 | Karasawa et al. |
| 2009/0322864 A1 | 12/2009 | Karasawa et al. |
| 2010/0010294 A1 | 1/2010 | Conlon et al. |
| 2010/0010298 A1 | 1/2010 | Bakos et al. |
| 2010/0010303 A1 | 1/2010 | Bakos |
| 2010/0016878 A1 | 1/2010 | Smith |
| 2010/0023032 A1 | 1/2010 | Granja Filho |
| 2010/0036198 A1 | 2/2010 | Tacchino et al. |
| 2010/0048990 A1 | 2/2010 | Bakos |
| 2010/0049223 A1 | 2/2010 | Granja Filho |
| 2010/0056862 A1 | 3/2010 | Bakos |
| 2010/0076451 A1 | 3/2010 | Zwolinski et al. |
| 2010/0081875 A1 | 4/2010 | Fowler et al. |
| 2010/0113872 A1 | 5/2010 | Asada et al. |
| 2010/0121362 A1 | 5/2010 | Clague et al. |
| 2010/0130817 A1 | 5/2010 | Conlon |
| 2010/0152539 A1 | 6/2010 | Ghabrlal et al. |
| 2010/0152725 A1 | 6/2010 | Pearson et al. |
| 2010/0160906 A1 | 6/2010 | Jarrard |
| 2010/0191050 A1 | 7/2010 | Zwolinski |
| 2010/0191267 A1 | 7/2010 | Fox |
| 2010/0198248 A1 | 8/2010 | Vakharia |
| 2010/0210906 A1 | 8/2010 | Wendlandt |
| 2010/0217367 A1 | 8/2010 | Belson |
| 2010/0229610 A1 | 9/2010 | Garrigan et al. |
| 2010/0249700 A1* | 9/2010 | Spivey ............ A61B 17/00234 604/96.01 |
| 2010/0268025 A1 | 10/2010 | Belson |
| 2010/0280368 A1 | 11/2010 | Can et al. |
| 2010/0286791 A1 | 11/2010 | Goldsmith |
| 2010/0298642 A1 | 11/2010 | Trusty et al. |
| 2010/0312056 A1 | 12/2010 | Galperin et al. |
| 2010/0331622 A2 | 12/2010 | Conlon |
| 2011/0077476 A1 | 3/2011 | Rofougaran et al. |
| 2011/0087223 A1* | 4/2011 | Spivey ............ A61B 18/14 606/49 |
| 2011/0087224 A1 | 4/2011 | Cadeddu et al. |
| 2011/0087265 A1* | 4/2011 | Nobis ............ A61B 17/29 606/205 |
| 2011/0093009 A1 | 4/2011 | Fox |
| 2011/0098694 A1 | 4/2011 | Long |
| 2011/0098704 A1 | 4/2011 | Long et al. |
| 2011/0112434 A1 | 5/2011 | Ghabrlal et al. |
| 2011/0112527 A1 | 5/2011 | Hamilton, Jr. et al. |
| 2011/0115891 A1 | 5/2011 | Trusty |
| 2011/0130751 A1 | 6/2011 | Malis et al. |
| 2011/0152610 A1 | 6/2011 | Trusty et al. |
| 2011/0152878 A1 | 6/2011 | Trusty et al. |
| 2011/0152923 A1 | 6/2011 | Fox |
| 2011/0160514 A1 | 6/2011 | Long et al. |
| 2011/0190764 A1 | 8/2011 | Long et al. |
| 2011/0224663 A1 | 9/2011 | Heim et al. |
| 2011/0237890 A1* | 9/2011 | Farritor ............ A61B 34/73 600/142 |
| 2011/0245619 A1 | 10/2011 | Holcomb |
| 2011/0284014 A1 | 11/2011 | Cadeddu et al. |
| 2011/0288547 A1 | 11/2011 | Morgan et al. |
| 2011/0306840 A1 | 12/2011 | Allen et al. |
| 2011/0313415 A1 | 12/2011 | Fernandez et al. |
| 2012/0005939 A1 | 1/2012 | Vandewalle |
| 2012/0050511 A1* | 3/2012 | Takahashi ............ A61B 1/00114 348/65 |
| 2012/0088965 A1 | 4/2012 | Stokes et al. |
| 2012/0089089 A1 | 4/2012 | Swain et al. |
| 2012/0089093 A1 | 4/2012 | Trusty |
| 2012/0101331 A1 | 4/2012 | Gilad et al. |
| 2012/0101413 A1 | 4/2012 | Beetel et al. |
| 2012/0116155 A1 | 5/2012 | Trusty |
| 2012/0116266 A1 | 5/2012 | Houser et al. |
| 2012/0149981 A1 | 6/2012 | Khait et al. |
| 2012/0191075 A1 | 7/2012 | Trusty |
| 2012/0197246 A1 | 8/2012 | Mauch |
| 2012/0209070 A1* | 8/2012 | Piech ............ A61B 17/0293 600/110 |
| 2012/0239082 A1* | 9/2012 | Shelton, IV ......... A61B 17/072 606/206 |
| 2013/0030430 A1 | 1/2013 | Stewart et al. |
| 2013/0030462 A1* | 1/2013 | Keating ............ A61B 17/0218 606/206 |
| 2013/0090666 A1 | 4/2013 | Hess et al. |
| 2013/0158348 A1* | 6/2013 | Nobis ............ A61B 1/00158 600/109 |
| 2013/0245356 A1 | 9/2013 | Fernandez et al. |
| 2013/0267834 A1 | 10/2013 | McGee |
| 2013/0331646 A1* | 12/2013 | Pell ............ A61B 17/29 600/106 |
| 2013/0331649 A1 | 12/2013 | Khait et al. |
| 2014/0014024 A1 | 1/2014 | Schroeder |
| 2014/0052216 A1 | 2/2014 | Long et al. |
| 2014/0121678 A1 | 5/2014 | Trusty et al. |
| 2015/0157293 A1* | 6/2015 | Shibamoto ............ A61B 8/4455 600/462 |
| 2017/0049508 A1 | 2/2017 | Long et al. |
| 2017/0119465 A1 | 5/2017 | Long et al. |
| 2018/0303541 A1 | 10/2018 | Long et al. |
| 2018/0360535 A1 | 12/2018 | Long et al. |
| 2019/0053805 A1 | 2/2019 | Harris et al. |
| 2019/0321073 A1 | 10/2019 | Griffith et al. |

FOREIGN PATENT DOCUMENTS

| | | |
|---|---|---|
| DE | 19757056 B4 | 8/2008 |
| DE | 102006027873 B4 | 10/2009 |
| EP | 0086338 A1 | 8/1983 |
| EP | 0286415 A2 | 10/1988 |
| EP | 0589454 A2 | 3/1994 |
| EP | 1281356 A2 | 2/2003 |
| EP | 0941128 B1 | 10/2004 |
| EP | 0848598 B1 | 2/2005 |
| EP | 1281360 B1 | 3/2005 |
| EP | 1153578 B1 | 3/2007 |
| EP | 1493397 B1 | 9/2011 |
| FR | 2731610 A1 | 9/1996 |
| GB | 330629 A | 6/1930 |
| JP | S63309252 A | 12/1988 |
| JP | H0438960 A | 2/1992 |
| JP | H0829699 A | 2/1996 |
| JP | H0975365 A | 3/1997 |
| JP | H1024049 A | 1/1998 |
| JP | 3007713 B2 | 2/2000 |
| JP | 2000245683 A | 9/2000 |
| JP | 2001526072 A | 12/2001 |
| JP | 2002369791 A | 12/2002 |
| JP | 2003088494 A | 3/2003 |
| JP | 2003235852 A | 8/2003 |
| JP | 2004033525 A | 2/2004 |
| JP | 2004065745 A | 3/2004 |
| JP | 2005121947 A | 5/2005 |
| JP | 2005261514 A | 9/2005 |
| JP | 2005296063 A | 10/2005 |
| JP | 2006297005 A | 11/2006 |
| JP | 2006343510 A | 12/2006 |
| JP | 2007125264 A | 5/2007 |
| JP | 5646674 B2 | 12/2014 |
| NL | 1021295 C2 | 2/2004 |
| SU | 194230 | 5/1967 |
| SU | 980703 A1 | 12/1982 |
| WO | WO-8607543 A1 | 12/1986 |
| WO | WO-9320765 A1 | 10/1993 |
| WO | WO-9712557 A1 | 4/1997 |

(56) References Cited

FOREIGN PATENT DOCUMENTS

| | | |
|---|---|---|
| WO | WO-9900060 A1 | 1/1999 |
| WO | WO-9917661 A1 | 4/1999 |
| WO | WO-9930622 A2 | 6/1999 |
| WO | WO-0126708 A1 | 4/2001 |
| WO | WO-0158360 A2 | 8/2001 |
| WO | WO-03081761 A2 | 10/2003 |
| WO | WO-2005018467 A2 | 3/2005 |
| WO | WO-2007013059 A2 | 2/2007 |
| WO | WO-2008102154 A2 | 8/2008 |
| WO | WO-2008151237 A1 | 12/2008 |
| WO | WO-2009029065 A1 | 3/2009 |
| WO | WO-2009032623 A2 | 3/2009 |

OTHER PUBLICATIONS

Guido M. Sclabas, M.D., et al., "Endoluminal Methods for Gastrotomy Closure in Natural Orifice TransEnteric Surgery (NOTES)," Surgical Innovation, vol. 13, No. 1, pp. 23-30, Mar. 2006.

Fritscher-Ravens, et al., "Transgastric Gastropexy and Hiatal Hernia Repair for GERD Under EUS Control: a Porcine Model," Gastrointestinal Endoscopy, vol. 59, No. 1, pp. 89-95, 2004.

Kennedy, et al., "High-Burst-Strength, Feedback-Controlled Bipolar Vessel Sealing," Surgical Endoscopy, vol. 12, pp. 876-878 (1998).

Collins et al., "Local Gene Therapy of Solid Tumors with GM-CSF and B7-1 Eradicates Both Treated and Distal Tumors," Cancer Gene Therapy, vol. 13, pp. 1061-1071 (2006).

K. Sumiyama et al., "Transesophageal Mediastinoscopy by Submucosal Endoscopy With Mucosal Flap Safety Value Technique," Gastrointest Endosc., Apr. 2007, vol. 65(4), pp. 679-683 (Abstract).

K. Sumiyama et al., "Submucosal Endoscopy with Mucosal Flap Safety Valve," Gastrointest Endosc. Apr. 2007, vol. 65(4) pp. 694-695 (Abstract).

K. Sumiyama et al., "Endoscopic Caps," Tech. Gastrointest. Endosc., vol. 8, pp. 28-32, 2006.

Z-Offset Technique Used in the Introduction of Trocar During Laparoscopic Surgery, M.S. Hershey NOTES Presentation to EES NOTES Development Team, Sep. 27, 2007.

I. Fraser, "An Historical Perspective on Mechanical Aids in Intestinal Anastamosis," Surg. Gynecol. Obstet. (Oct. 1982), vol. 155, pp. 566-574.

C. Cope, "Creation of Compression Gastroenterostomy by Means of the Oral, Percutaneous, or Surgical Introduction of Magnets: Feasibility Study in Swine," J. Vasc Interv Radiol, (1995), vol. 6(4), pp. 539-545.

N. Chopita et al., "Endoscopic Gastroenteric Anastamosis Using Magnets," Endoscopy, (2005), vol. 37(4), pp. 313-317.

H. Okajima et al., "Magnet Compression Anastamosis for Bile Duct Stenosis After Duct to Duct Biliary Reconstruction in Living Donor Liver Transplantation," Liver Transplantation (2005), pp. 473-475.

T. Handy, Jr., M.D et al., "A Biofragmentable Ring for Sutureless Bowel Anastomosis. An Experimental Study," Dis Col Rectum, (1985), vol. 28, pp. 484-490.

P. O'Neill, M.D et al., "Nonsuture Intestinal Anastomosis," Am J. Surg, (1962), vol. 104, pp. 761-767.

J.B. Murphy, M.D., "Cholecysto-Intestinal, Gastro-Intestinal, Entero-Intestinal Anastomosis, and Approximation Without Sutures (original research)," Med Rec, (Dec. 10, 1892), vol. 42(24), pp. 665-676.

B. Rubinsky, Ph.D., "Irreversible Electroporation in Medicine," Technology in Cancer Research and Treatment, vol. 6, No. 4, August (2007), pp. 255-259.

D.B. Nelson, MD et al., "Endoscopic Hemostatic Devices," Gastrointestinal Endoscopy, vol. 54, No. 6, 2001, pp. 833-840.

CRE™ Pulmonary Balloon Dilator; [online] URL: http://www.bostonscientific.com/Device.bsci?page=HCP_Overview&navReIId=1000.1003&method=D . . . , accessed Jul. 18, 2008 (4 pages).

H. Seifert, et al., "Retroperitoneal Endoscopic Debridement for Infected Peripancreatic Necrosis," The Lancet, Research Letters, vol. 356, Aug. 19, 2000, pp. 653-655.

D. Wilhelm et al., "An Innovative, Safe and Sterile Sigmoid Access (ISSA) for NOTES," Endoscopy 2007, vol. 39, pp. 401-406.

Wong et al., "Combined Percutaneous Radiofrequency Ablation and Ethanol Injection for Hepatocellular Carcinoma in High-Risk Locations," AJR, 190, pp. W187-W195 (2008).

Heller et al., "Electrically mediated plasmid DNA delivery to hepatocellular carcinomas in vivo," Gene Therapy, 7, pp. 826-829 (2000).

Widera et al., "Increased DNA Vaccine Delivery and Immunogenicity by Electroporation In Vivo," The Journal of Immunology, 164, pp. 4635-4640 (2000).

Weaver et al., "Theory of electroporation: A review," Bioelectrochemistry and Bioenergetics, 41, pp. 135-160 (1996).

Guyton et al., "Membrane Potentials and Action Potentials," W.B. Sanders, ed. Textbook of Medical Physiology, p. 56 (2000).

Guyton et al., "Contraction of Skeletal Muscle," Textbook of Medical Physiology, pp. 82-84 (2000).

Zadno et al., "Linear Superelasticity in Cold-Worked NI-TI," Engineering Aspects of Shape Memory Alloys, pp. 414-419 (1990).

How Stuff Works "How Smart Structures Will Work," http://science.howstuffworks.com/engineering/structural/smart-structure1.htm; accessed online Nov. 1, 2011 (3 pages).

Bewlay et al., "Spinning" in ASM Handbook, vol. 14B, Metalworking: Sheet Forming (2006).

Schoenbach et al. "Bacterial Decontamination of Liquids with Pulsed Electric Fields" IEEE Transactions on Dielectrics and Electrical Insulation. vol. 7 No. 5. Oct. 2000, pp. 637-645.

Davalos, et al., "Tissue Ablation with Irreversible Electroporation," Annals of Biomedical Engineering, 33.2 (2005): 223-231.

"Ethicon Endo-Surgery Novel Investigational Notes and SSL Devices Featured in 15 Presentations at Sages," Apr. 22, 2009 Press Release; URL http://www.jnj.com/connect/news/all/20090422_152000; accessed Aug. 28, 2009 (3 pages).

D.G. Fong et al., "Transcolonic Ventral Wall Hernia Mesh Fixation in a Porcine Model," Endoscopy 2007; 39: 865-869.

J.D. Paulson, M.D., et al., "Development of Flexible Culdoscopy," The Journal of the American Association of Gynecologic Laparoscopists, Nov. 1999, vol. 6, No. 4, pp. 487-490.

C. Cope et al., "Long Term Patency of Experimental Magnetic Compression Gastroenteric Anastomoses Achieved with Covered Stents," Gastrointest Endosc, (2001), vol. 53, pp. 780-784.

K. Sumiyama et al., "Transgastric Cholecystectomy: Transgastric Accessibility to the Gallbladder Improved with the SEMF Method and a Novel Multibending Therapeutic Endoscope," Gastrointest Endosc., Jun. 2007, vol. 65(7), pp. 1028-1034 (Abstract).

C.P. Swain, M.D et al., "Anastomosis at Flexible Endoscopy: An Experimental Study of Compression Button Gastrojejunostomy," Gastrointest Endosc, (1991), vol. 37, pp. 628-632.

Printout of web page—http://www.vacumed.com/zcom/product/Product.do?compid=27&prodid=852, #51XX Low-Cost Permanent Tubes 2MM ID, Smooth Interior Walls, VacuMed, Ventura, California, Accessed Jul. 24, 2007.

Endoscopic Retrograde Cholangiopancreatogram (ERCP); [online] URL: http://www.webmd.com/digestive-disorders/endoscopic-retrograde-cholangiopancreatogram-ercp.htm; last updated: Apr. 30, 2007; accessed: Feb. 21, 2008 (6 pages).

Link et al., "Regional Chemotherapy of Nonresectable Colorectal Liver Metastases with Mitoxanthrone, 5-Fluorouracil, Folinic Acid, and Mitomycin C May Prolong Survival," Cancer, 92, pp. 2746-2753 (2001).

Instant Armor: Science Videos -Science News -ScienCentral; http://www.sciencentral.com/articles./view.php3?article_id=218392121; accessed online Nov. 1, 2011 (2 pages).

Mulier et al., "Radiofrequency Ablation Versus Resection for Resectable Colorectal Liver Metastases: Time for a Randomized Trial?" Annals of Surgical Oncology, 15(1), pp. 144-157 (2008).

Edd, et al., "In Vivo Results of a New Focal Tissue Ablation Technique: Irreversible Electroporation," IEEE Trans Biomed Eng, vol. 53, pp. 1409-1415, 2006.

Ogando, "Prototype Tools That Go With the Flow," Design News, 2 pages, Jul. 17, 2006.

(56) References Cited

OTHER PUBLICATIONS

M.E. Ryan et al., "Endoscopic Intervention for Biliary Leaks After Laparoscopic Cholecystectomy: A Multicenter Review," Gastrointest. Endosc., vol. 47(3), 1998, pp. 261-266.
J.W. Hazey et al., "Natural Orifice Transgastric Endoscopic Peritoneoscopy in Humans: Initial Clinical Trial," Surg Endosc, (Jan. 2008), vol. 22(1), pp. 16-20.
A. Fritscher-Ravens et al., "Transluminal Endosurgery: Single Lumen Access Anastamotic Device for Flexible Endoscopy," Gastrointestinal Endosc, (2003), vol. 58(4), pp. 585-591.
ERCP; Jackson Siegelbaum Gastroenterology; [online] URL: http://www.gicare.com/pated/epdgs20.htm; accessed Feb. 21, 2008 (3 pages).
Ethicon, Inc., "Wound Closure Manual: Chapters (The Surgical Needle)," 15 pages, (1994).
USGI® EndoSurgical Operating System—g-Prox® Tissue Grasper/Approximation Device; [online] URL: http://www.usglmedical.com/eos/components-gprox.htm—accessed May 30, 2008 (2 pages).
Nakazawa et al., "Radiofrequency Ablation of Hepatocellular Carcinoma: Correlation Between Local Tumor Progression After Ablation and Ablative Margin," AJR, 188, pp. 480-488 (Feb. 2007).
Miklavcic et al., "A validated model of in vivo electric field distribution in tissues for electrochemotherapy and for DNA electrotransfer for gene therapy," Biochimica et Biophysica Acta, 1523, pp. 73-83 (2000).
Evans, "Ablative and cathether-delivered therapies for colorectal liver metastases (CRLM)," EJSO, 33, pp. S64-S75 (2007).
"Ethicon Endo-Surgery Studies Presented at DDW Demonstrate Potential of Pure NOTES Surgery With Company's Toolbox," Jun. 3, 2009 Press Release; URL http://www.jnj.com/connect/news/product/20090603_120000; accessed Aug. 28, 2009 (3 pages).
Castellvi et al., "Hybrid Transvaginal NOTES Sleeve Gastrectomy in a Porcine Model Using a Magnetically Anchored Camera and Novel Instrumentation," Abstract submitted along with Poster at SAGES Annual Meeting in Phoenix, AZ, Apr. 22, 2009 (1 page).
OCTO Port Modular Laparoscopy System for Single Incision Access, Jan. 4, 2010; URL http://www.medgadget.com/archives/2010/01/octo_port_modular_laparo . . . ; accessed Jan. 5, 2010 (4 pages).
Hakko Retractors, obtained Aug. 25, 2009 (5 pages).
Castellvi et al., "Hybrid Transvaginal NOTES Sleeve Gastrectomy in a Porcine Model Using a Magnetically Anchored Camera and Novel Instrumentation," Poster submitted along with Abstract at SAGES Annual Meeting in Phoenix, AZ, Apr. 22, 2009 (1 page).
Stanway, Smart Fluids: Current and Future Developments. Material Science and Technology, 20, pp. 931-939, 2004; accessed online Nov. 1, 2011 at http://www.dynamics.group.shef.ac.uk/smart/smart.html (7 pages).
Rutala et al. "Guideline for Disinfection and Sterilization in Healthcare Facilities, 2008" (available at http://www.cdc.gov/hicpac/Disinfection_Sterilization/13_11sterilizingPractices.html).
G.A. Hallenbeck, M.D et al., "An Instrument for Colorectal Anastomosis Wthout Sutrues," Dis Col Rectum, (1963), vol. 5, pp. 98-101.
Maxim Integrated Application Note 3977: Class D Amplifiers: Fundamentals of Operation and Recent Developments, Jan. 31, 2007.
Jolly et al., Properties and Applications of Commercial Magneto rheological Fluids. SPIE 5th Annual Int. Symposium on Smart Structures and Materials, 1998 (18 pages).
F.N. Denans, Nouveau Procede Pour La Guerison Des Plaies Des Intestines. Extrait Des Seances De La Societe Royale De Medecine De Marseille, Pendant Le Mois De Decembre 1825, et le Premier Tremestre De 1826, Séance Du 24 Fevrier 1826. Recueil De La Societe Royale De Medecin De Marseille. Marseille: Impr. D'Achard, 1826; 1:127-31. (with English translation).
K.E. Mönkemüller, M.D., et al., "Transmural Drainage of Pancreatic Fluid Collections Without Electrocautery Using the Seidinger Technique," Gastrointestinal Endoscopy, vol. 48, No. 2, 1998, pp. 195-200, (Received Oct. 3, 1997; Accepted Mar. 31, 1998).

\* cited by examiner

SYSTEM FOR PERFORMING A MINIMALLY INVASIVE SURGICAL PROCEDURE

CROSS-REFERENCE TO RELATED APPLICATION

This application is a divisional application claiming priority under 35 U.S.C. § 121 to U.S. patent application Ser. No. 13/778,582, entitled SYSTEM FOR PERFORMING A MINIMALLY INVASIVE SURGICAL PROCEDURES, filed on Feb. 27, 2013, now U.S. Patent Application Publication No. 2014/0243597, the entire disclosure of which is hereby incorporated by reference herein.

BACKGROUND OF THE INVENTION

Surgical procedures are often used to treat and cure a wide range of diseases, conditions, and injuries. Surgery often requires access to internal tissue through open surgical procedures or endoscopic surgical procedures. The term "endoscopic" refers to all types of minimally invasive surgical procedures including laparoscopic, arthroscopic, natural orifice intraluminal, and natural orifice transluminal procedures. Endoscopic surgery has numerous advantages compared to traditional open surgical procedures, including reduced trauma, faster recovery, reduced risk of infection, and reduced scarring. Endoscopic surgery is often performed with an insufflatory fluid present within the body cavity, such as carbon dioxide or saline, to provide adequate space to perform the intended surgical procedures. The insufflated cavity is generally under pressure and is sometimes referred to as being in a state of pneumoperitoneum. Surgical access devices are often used to facilitate surgical manipulation of internal tissue while maintaining pneumoperitoneum. For example, trocars are often used to provide a port through which endoscopic surgical instruments are passed. Trocars generally have an instrument seal, which prevents the insufflatory fluid from escaping while an instrument is positioned in the trocar.

Other camera and surgical tool guiding systems have been disclosed. For example, Magnetic anchoring and guidance systems (MAGS) have been developed for use in minimally invasive procedures. MAGS include an internal device attached in some manner to a surgical instrument, or camera or other viewing device, and an external hand held device or external control unit ("ECU") for controlling the movement of the internal device. Each of the external and internal devices has magnets, which are magnetically coupled to each other across, for example, a patient's abdominal wall. In the current systems, the external magnet may be adjusted by varying the height of the external magnet.

While surgical access devices are known, no one has previously made or used the surgical devices and methods in accordance with the present invention.

BRIEF DESCRIPTION OF THE FIGURES

The novel features of the various embodiments of the invention are set forth with particularity in the appended claims. The various embodiments of the invention, however, both as to organization and methods of operation, together with further objects and advantages thereof, may best be understood by reference to the following description, taken in conjunction with the accompanying drawings in which:

DETAILED DESCRIPTION

Figure 1:
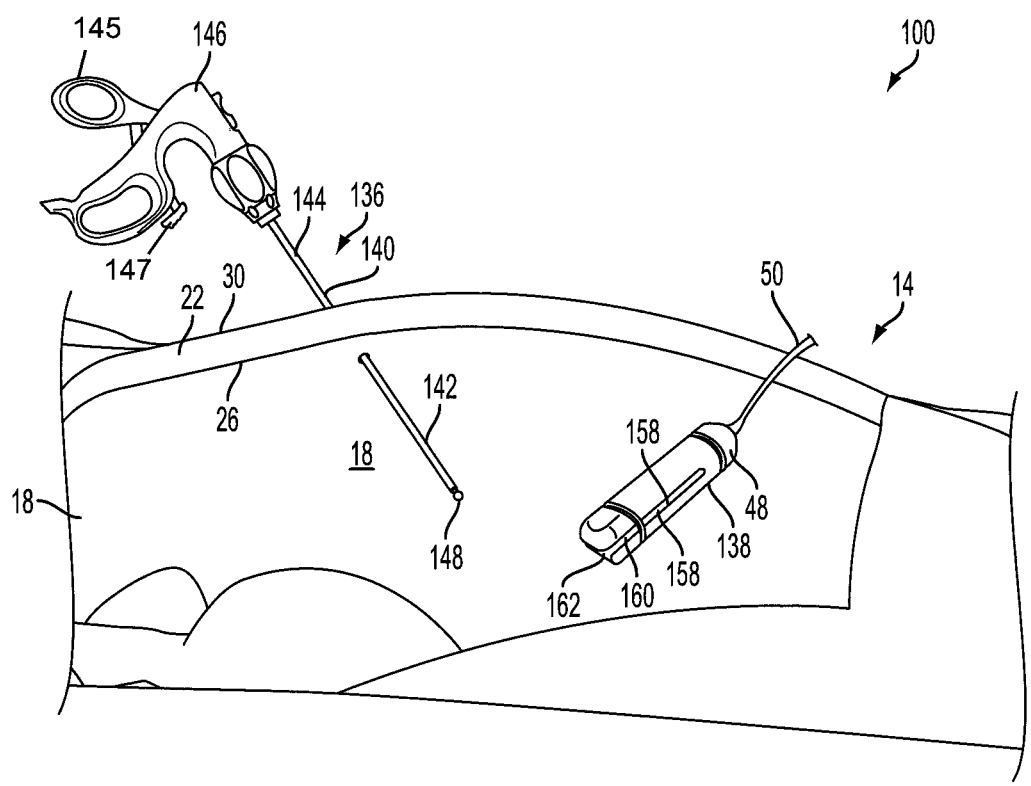
FIG. 1 is schematic view of a patient's body cavity showing a percutaneous member extended through a wall of the cavity and an in-vivo instrument in accordance with at least one embodiment.

Numerous specific details are set forth to provide a thorough understanding of the overall structure, function, manufacture, and use of the embodiments as described in the specification and illustrated in the accompanying drawings. It will be understood by those skilled in the art, however, that the embodiments may be practiced without such specific details. In other instances, well-known operations, components, and elements have not been described in detail so as not to obscure the embodiments described in the specification. Those of ordinary skill in the art will understand that the embodiments described and illustrated herein are non-limiting examples, and thus it can be appreciated that the specific structural and functional details disclosed herein may be representative and do not necessarily limit the scope of the embodiments, the scope of which is defined solely by the appended claims.

Reference throughout the specification to "various embodiments or forms," "some embodiments or forms," "one embodiment or form," or "an embodiment", or the like, means that a particular feature, structure, or characteristic described in connection with the embodiment is included in at least one embodiment or form. Thus, appearances of the phrases "in various embodiments," "in some embodiments," "in one embodiment," or "in an embodiment", or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features structures, or characteristics of one or more other embodiments without limitation.

It will be appreciated that the terms "proximal" and "distal" may be used throughout the specification with reference to a clinician manipulating one end of an instrument used to treat a patient. The term "proximal" refers to the portion of the instrument closest to the clinician and the term "distal" refers to the portion located farthest from the clinician. It will be further appreciated that for conciseness and clarity, spatial terms such as "vertical," "horizontal," "up," and "down" may be used herein with respect to the illustrated embodiments. However, surgical instruments may be used in many orientations and positions, and these terms are not intended to be limiting and absolute.

The term "coupled" is defined as connected, although not necessarily directly, and not necessarily mechanically; two items that are "coupled" may be integral with each other. The terms "a" and "an" are defined as one or more unless this disclosure explicitly requires otherwise.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a surgical system, device, or apparatus that "comprises," "has," "includes" or "contains" one or more elements possesses those one or more elements, but is not limited to possessing only those one or more elements. Likewise, an element of a system, device, or apparatus that "comprises," "has," "includes" or "contains" one or more features possesses those one or more features, but is not limited to possessing only those one or more features.

As used herein, the term "percutaneous" refers to any medical procedure where access to inner organs or other tissue is done via a puncture of the skin, rather than by using an "open" approach where inner organs or tissue are exposed.

Referring primarily to FIG. 1, a surgical device 100 is shown in conjunction with a patient 14, and more particularly relative to a longitudinal cross-sectional view of the ventral cavity of the patient. For brevity, cavity 18 is shown in a simplified conceptual form without organs and the like. Cavity 18 is at least partially defined by a wall 22, such as the abdominal wall, that includes an interior surface 26 and an exterior surface 30. The exterior surface 30 of wall 22 can also be an exterior surface of the patient 14.

Further to the above, although surgical device 100 is depicted relative to ventral cavity 18, surgical device 100 and various other embodiments of the present disclosure can be utilized in other body cavities of a patient, human or animal, such as, for example, the thoracic cavity, the abdominopelvic cavity, the abdominal cavity, the pelvic cavity, and other cavities (e.g., lumens of organs such as the stomach, colon, or bladder of a patient). In some embodiments of the present methods, and when using embodiments or forms of the present devices and systems, a pneumoperitoneum may be created in the cavity of interest to yield a relatively open space within the cavity.

The surgical device 100 may comprise an in-vivo instrument 138 and a percutaneous member 136. The in-vivo instrument 138 can be inserted or introduced into cavity 18 through an access port (not shown) having a suitable internal diameter. Such access ports include those created using a conventional laparoscopic trocar, gel ports, and those created by incision (e.g., abdominal incision). In-vivo instrument 138 can be pushed through the access port with any elongated instrument such as, for example, a surgical instrument such as a laparoscopic grasper. If the cavity 18 is pressurized, in-vivo instrument 138 can be inserted or introduced into the cavity 18 before or after the cavity is pressurized. The in-vivo instrument 138 may also be inserted into the cavity 18 via an introducer tool. Several types of introducers that may be utilized, for example, are described in U.S. application Ser. No. 13/325,791, entitled INTRODUCER FOR AN INTERNAL MAGNETIC CAMERA, filed Dec. 14, 2011, the entire disclosure of which is incorporated herein by reference.

Figure 2:
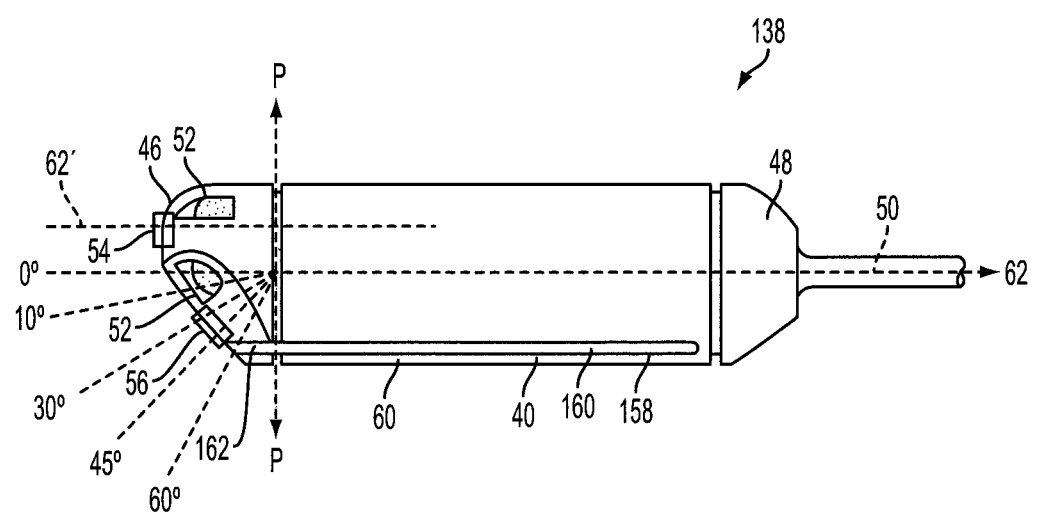
FIG. 2 is a side elevational view of an in-vivo instrument in accordance with at least one embodiment.

Referring to FIG. 2, the in-vivo instrument 138 may include a housing 40 which may include a central longitudinal axis 62 through the length of the housing 40, a body portion 60, shown as generally tubular in shape, a leading head portion 46, and a trailing end portion 48. Housing 40 may include at least one camera and at least one light emitting diode (LED). In the embodiment of housing 40 shown in FIG. 2, there are two LEDs 52 for each of the two cameras 54 and 56 on head portion 46.

For purposes of orientation, Referring again to FIG. 2, there is a plane P perpendicular to the longitudinal axis 62, between the body portion 60 and the head portion 46 of the housing 40. For purposes of orientation, the orientation of the lens of each of the cameras 54 and 56 is described herein as being directed or directed at angles relative to the axis 62 and plane P.

Referring still to FIG. 2, the camera 56 may have a lens that is directed at an angle greater than 0° and less than 90° and preferably between 10° to 60°, more preferably between 10° to 45°, measured downwardly, or distally, from the longitudinal axis 62 for viewing tissue under the axis 62 of the housing 40. For example, the angle of the camera 56 lens relative to the central axis 62 is directed between 20° and 40°, and more preferably between about 25° and 35°, and most preferably at or about 30°. The housing 40 may have in addition, a camera 54 having a lens aligned with the axis 62 or with a line parallel to it, at or about 0 degrees along the axis 62 for viewing sites directly in front of the housing 40. Those skilled in the art will appreciate that the cameras 54, 56 as used in the housing 40 may be any known optical viewing systems, such as, without limitation, standard cameras and lights, or fiber optic systems, or CCD systems, for example.

Referring still to FIG. 2, a tether 50 may extend from the trailing end 48 of the housing 40. The tether 50 may be, for example, an energy tether, such as an insulated electrical wire that extends from the trailing end 48 of the housing 40 for connection with an energy source (not shown). Tether 50 may also carry video images to a video screen outside of the patient. In use, when the housing 40 is deployed in a patient during a minimally invasive surgical or diagnostic procedure, the tether 50 would typically pass through a port (not shown) from the inside to the outside of a patient's body directly, or indirectly through an intermediate instrument, to an energy source or a receiver or processor for receiving video signals from the one or more cameras. Alternatively, the camera may be powered wirelessly or by internal batteries. Furthermore, the camera feed may be transmitted wirelessly to a receiver outside the patient where the signal can be viewed on an external monitor.

Referring again to FIG. 2, the housing 40 may include a cleaning apparatus to clean a dirty or obstructed lens as needed. A cleaning apparatus that may be utilized is described in U.S. patent application Ser. No. 13/399,358, entitled APPARATUS AND METHODS FOR CLEANING THE LENS OF AN ENDOSCOPE, filed Feb. 17, 2012, the entire disclosure of which is incorporated herein by reference. The cleaning apparatus may comprise a conduit having a lumen through which fluid flows. The conduit may extend through housing 40 and may comprise a distal tip, which may have a delivery port (not shown) such as an opening or a slot through which cleaning fluid may be directed toward camera 54 and/or camera 56.

Referring primarily to FIG. 1, the percutaneous member 136 may include an elongate body 140 which may have a distal portion 142 insertable into the cavity 18 through the wall 22 and a proximal portion 144 connected to a handle 146. The percutaneous member 136 may be releasably coupled to the in-vivo instrument 138, within the cavity 18, by operating the handle 146 as will be explained in more detail.

Referring again to FIG. 1, the percutaneous member 136 may be inserted into the cavity 18 by puncturing through wall 22. The elongate body 140 of the percutaneous member 136 may include an external needle with a piercing tip at a distal portion thereof for puncturing the wall 22 into the cavity 18. The elongate body 140 may be slidably disposed in the needle such that the piercing tip may be alternated between exposed and unexposed positions by sliding the elongate body 140 relative to the needle. For example, the piercing tip may be exposed by sliding the elongate body proximally relative to the needle. The piercing tip may then be utilized to puncture wall 22 into cavity 18. Once the distal portion 142 of the elongate body 140 passes into cavity 18, the piercing tip can be unexposed by sliding the elongate body 140 distally beyond the piercing tip thereby avoiding injury to surrounding internal tissue within the cavity 18.

Figure 3:
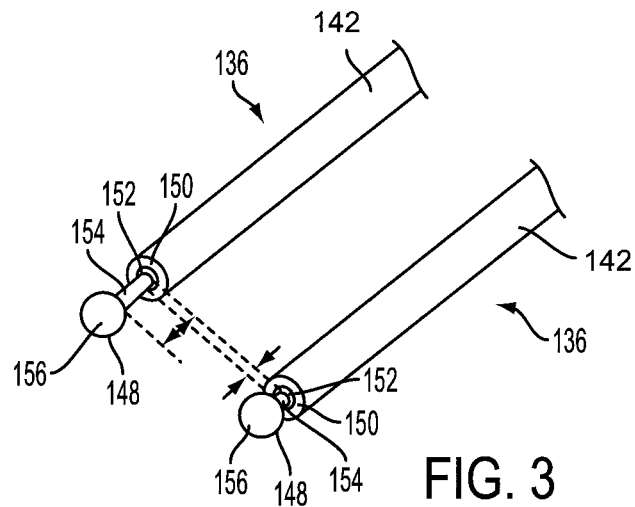
FIG. 3 depicts partial perspective views of an elongate body that includes a hollow tubular member and a connector that is movable from a partially extended position (on the left) to a partially retracted position (on the right) in accordance with at least one embodiment.

Referring primarily to FIG. 3, the elongate body 140 of the percutaneous member 136 may include a hollow tubular member 150 and a connector 148 that is slidably movable relative to the hollow tubular member 150. For example, the hollow tubular member 150 may include a lumen that extends therethrough and terminates at an opening 152 at a distal end thereof. In addition, the connector 148 may include an elongate shaft 154 such as, for example, a rod that is at least partially slidably disposed through the lumen of the hollow tubular member 150. Furthermore, the connector 148 may comprise an enlarged portion 156 at a distal end of the elongate shaft 154, as illustrated in FIG. 3.

Under certain circumstances, the enlarged portion 156 can be sized and shaped such that it cannot pass through the opening 152 of the hollow tubular member 150 when the connector 148 is slidably retracted relative to the hollow tubular member 150. In other words, the connector 148 may be retracted relative to the hollow tubular member 148 until the enlarged portion 156 is abutted against a distal end of the hollow tubular member 150. In one example, as illustrated in FIG. 3, the elongate shaft 154 may comprise a cylindrical, or substantially cylindrical, shape having a first diameter that is sized to allow the elongate shaft 154 to be slidably movable relative to the hollow tubular member 150. In addition, the enlarged portion 156 may comprise a spherical, or substantially spherical, shape that has a second diameter that is greater than the first diameter of the elongate shaft 154, such that the enlarged portion 156 is unable to be retracted through the opening 152 of the hollow tubular member 150.

Referring primarily to FIG. 2, the in-vivo instrument 138 may comprise a connection portion 158, which may include a track 160 that is, for example, substantially parallel to the axis 62 on a lateral section of body portion 60 of the in-vivo instrument 138. The track 160 may include an opening 162 at a distal portion thereof for entry into the track 160. The opening 162 may be sized to receive the enlarged portion 156 of the connector 148.

Figure 4:
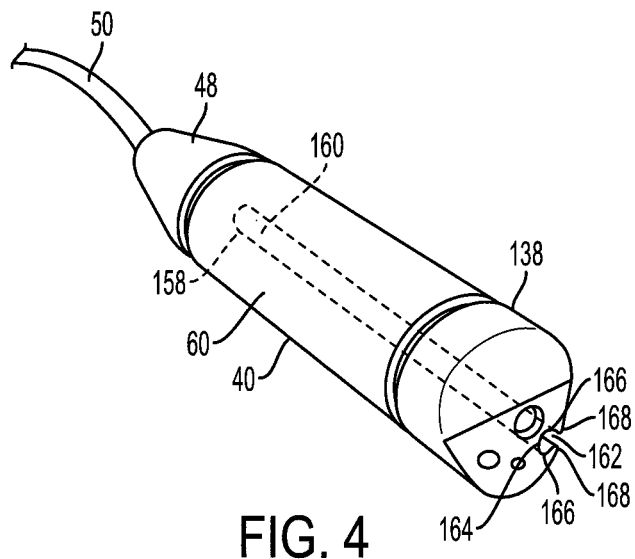
FIG. 4 is a perspective view of an in-vivo instrument in accordance with at least one embodiment.
Figure 5:
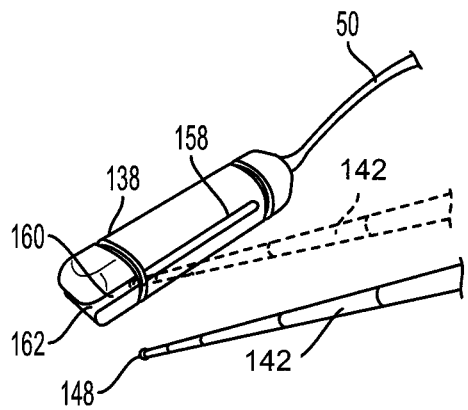
FIG. 5 is a perspective view of an in-vivo instrument and a connector prior to coupling engagement with the in-vivo instrument (in solid lines) and after coupling engagement with the in-vivo instrument (in broken lines)

Further to the above, referring to FIGS. 3-5, the enlarged portion 156 of the connector 148 may be operatively coupled to the track 160 through complementary contours, for example. A first contour of enlarged portion 156 can have a substantially matching shape to a second contour of track 160, such that the enlarged portion 156 may be inserted into and slid within track 160. For example, as illustrated in FIG. 4, the track 160 may comprise a generally "C-shaped" channel body that defines a semicircular channel when viewed in cross section. The channel body can include floor 164, upstanding sidewalls 166, and inwardly extending prongs 168. As described above, the enlarged portion 156 may have a spherical shape disposed at a distal end of the elongate shaft 154, which may have a cylindrical shape with a smaller diameter than the diameter of the enlarged portion 156. The enlarged portion 156 can be brought into sliding engagement with the C-shaped channel of the track 160 by inserting the enlarged portion 156 into the opening 162 of the track 160 while allowing the elongate shaft 154 to pass between prongs 168, as illustrated in FIG. 5. Once the enlarged portion 156 is received in the track 160, the in-vivo instrument 138 can be secured onto the percutaneous member 136 by retracting the elongate shaft 154 relative to the hollow tubular member 150 until the housing 40 of the in-vivo instrument 138 is abutted against the distal end of the hollow tubular member 150 to thereby lock a corresponding portion of the housing 40 between the enlarged portion 156 and the distal end of the hollow tubular member 150. Alternatively, the hollow tubular member 150 can be extended relative to the elongate shaft 154 until the in-vivo instrument 138 is abutted against the distal end of the hollow tubular member 150.

Referring primarily to FIG. 1, the handle 146 of the percutaneous member 136 may include a trigger 145 for retracting and/or extending the connector 148 relative to the hollow tubular member 150. A trigger lock 147 can be configured to selectively lock/unlock the trigger 145. For example, the trigger 145 of the handle 146 can be coupled to the elongate shaft 154 such that an operator may retract the elongate shaft 154 relative to the hollow tubular member 150 by moving the trigger 145. For example, the elongate shaft 154 can be retracted relative to the hollow tubular member 150 until the in-vivo instrument 138 is abutted against the distal end of the hollow tubular member 150. The operator may then lock the trigger 145 by pressing the trigger lock 147.

Further to the above, referring again to FIGS. 3-5, the connector 148 can be selectively locked to the in-vivo instrument 138 at a plurality of positions along a length of the track 160. For example, the connector 148 can be locked at a first position along the track 160 by guiding the enlarged portion 156 into the track 160, as described above, and advancing the enlarged portion 156 through the track 160 until the enlarged portion 156 reaches a desired first position. To lock connector 148 in the first position, the trigger 145 can be moved to retract the elongate shaft 154 relative to the hollow tubular member 150 until the in-vivo instrument 138 is abutted against the distal end of the hollow tubular member 150. The trigger lock 147 can then be pressed to lock the trigger 145 to prevent further movement of the connector 148 relative to the housing 40 of the in-vivo instrument 138.

To transition the enlarged portion 156 from the first position to another desired position or a "second" position along track 160, the trigger 145 may be unlocked by repressing the trigger lock 147. The trigger 145 may then be moved to advance the elongate shaft 154 relative to the hollow tubular member 150 thereby loosening the enlarged portion 156 in the track 160. The enlarged portion 156 can then be slidably moved to the second position, for example, by pushing the in-vivo instrument 138 against surrounding tissue of the patient. Upon reaching the second position, the trigger 145 can be moved again to retract the elongate shaft 154 relative to the hollow tubular member 150 to lock another corresponding portion of the housing 40 between the enlarged portion 156 and the distal end of the hollow tubular member 150. The trigger lock 147 can then be pressed to relock the trigger 145 to prevent further movement of the connector 148 relative to the housing 40 of the in-vivo instrument 138.

Referring to FIG. 3, the enlarged portion 156 can be selectively locked, for example, in a partially extended position (on the left) or in a partially retracted position (on the right). The elongate shaft 154 can be advanced or retracted relative to the hollow tubular member 150 by moving trigger 145 until a desired position is reached. The trigger lock 147 can then be pressed to lock the enlarged portion 156 in the desired position. The handle 146 may include visual indicators that may aid an operator in determining the position of the enlarged portion 156 relative to a distal end of the hollow tubular member 150, for example.

In various forms, one or both of track 160 and enlarged portion 156 can be made from a low friction, plastic material, such as polyethylene, Teflon®, or polypropylene to provide a low coefficient of friction between the members as they slide relative to one another. Furthermore, it will be understood that the track 160 and the enlarged portion 156 may be provided in various shapes and configurations that are complementary to the shape of track 160 to facilitate selective movement of the enlarged portion 156 and the locking of the connector 148 to the housing 40 when the connector 148 has been moved to the desired position.

Referring again to FIGS. 1 and 2, the connector 148 of the percutaneous member 136 can be coupled with the connection portion 158 of the in-vivo instrument 138 inside cavity 18. In some instances, to minimize the number of access ports in the wall 22, an operator may need to rely on the cameras 54 and 56 of the in-vivo instrument 138 to facilitate coupling of the connector 148 to the connection portion 158. For example, the camera 56 may be positioned adjacent the opening 162 of the track 160, as illustrated in FIG. 2, to allow the operator to view the approach of connector 148 and its subsequent coupling with the track 160. Relying on cameras 54 and/or 56 to couple the in-vivo instrument 138 to the percutaneous member 136 may result in the ability to reduce the number of access ports in the wall 22.

Figure 6:
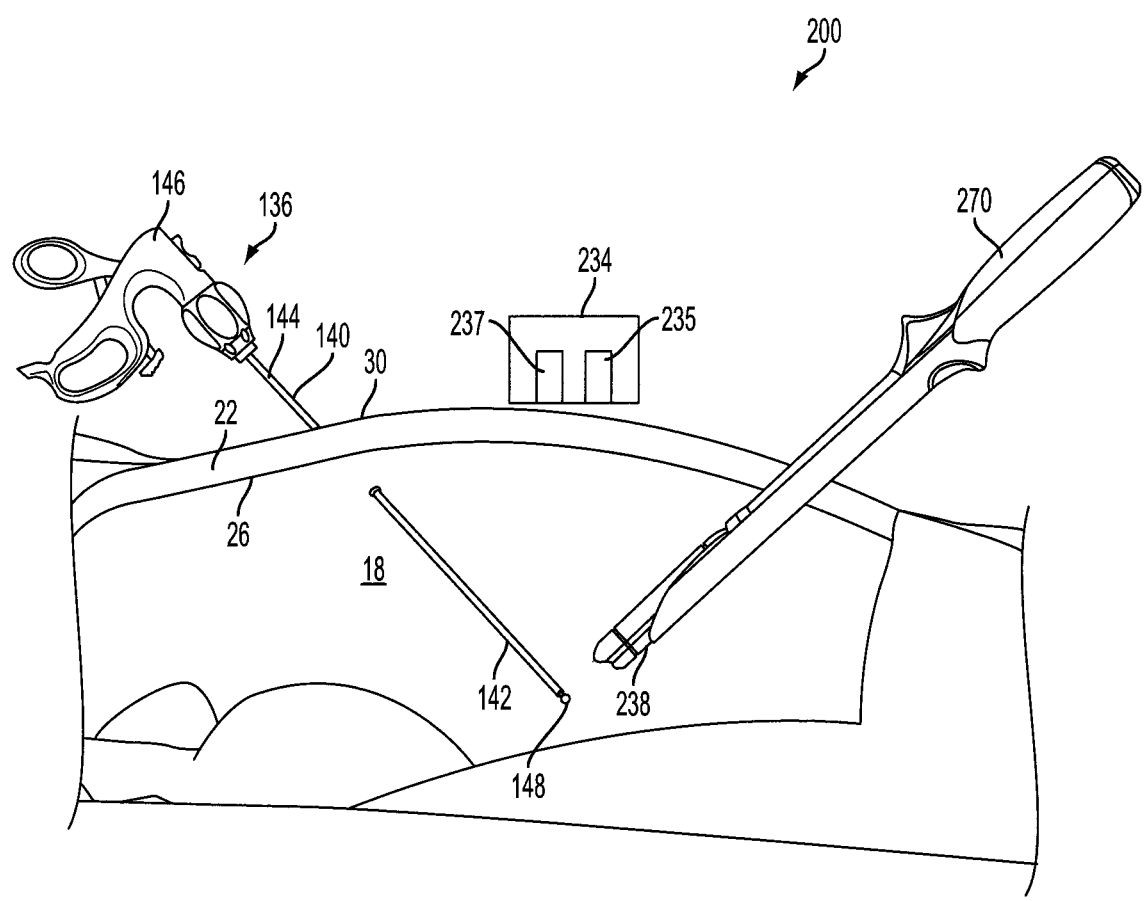
FIG. 6 is schematic view of a patient's body cavity and a surgical system in accordance with at least one embodiment.

Referring now to FIG. 6, a surgical system 200 for surgical procedures is shown in conjunction with a patient, and more particularly relative to a longitudinal cross-sectional view of the ventral cavity of the patient. As described above, the cavity 18 is shown in simplified conceptual form without organs and the like. Furthermore, the cavity 18 is at least partially defined by wall 22. The exterior surface of wall 22 can also be an exterior surface of the patient.

Referring primarily to FIG. 6, the surgical system 200, in at least one form, comprises an ex-vivo positioning mechanism 234, an in-vivo instrument 238, and a percutaneous member 136. The ex-vivo positioning mechanism 234 is configured to magnetically position in-vivo instrument 238 within the cavity 18. As illustrated in FIG. 6, the ex-vivo positioning mechanism 234 can be positioned outside the cavity 18 near, adjacent to, and/or in contact with the exterior surface of the wall 22.

Figure 6A:
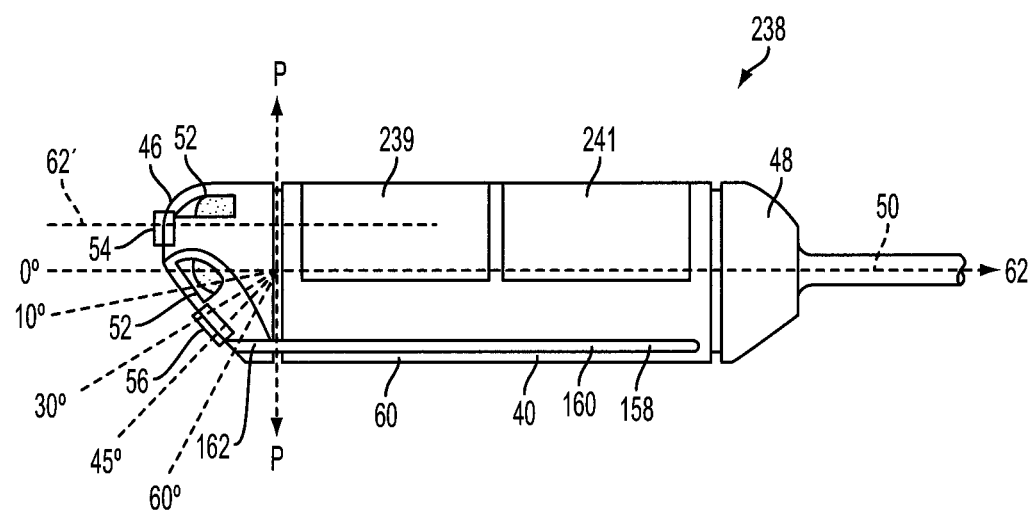
FIG. 6A is a side elevational view of an in-vivo instrument in accordance with at least one embodiment.
Figure 7:
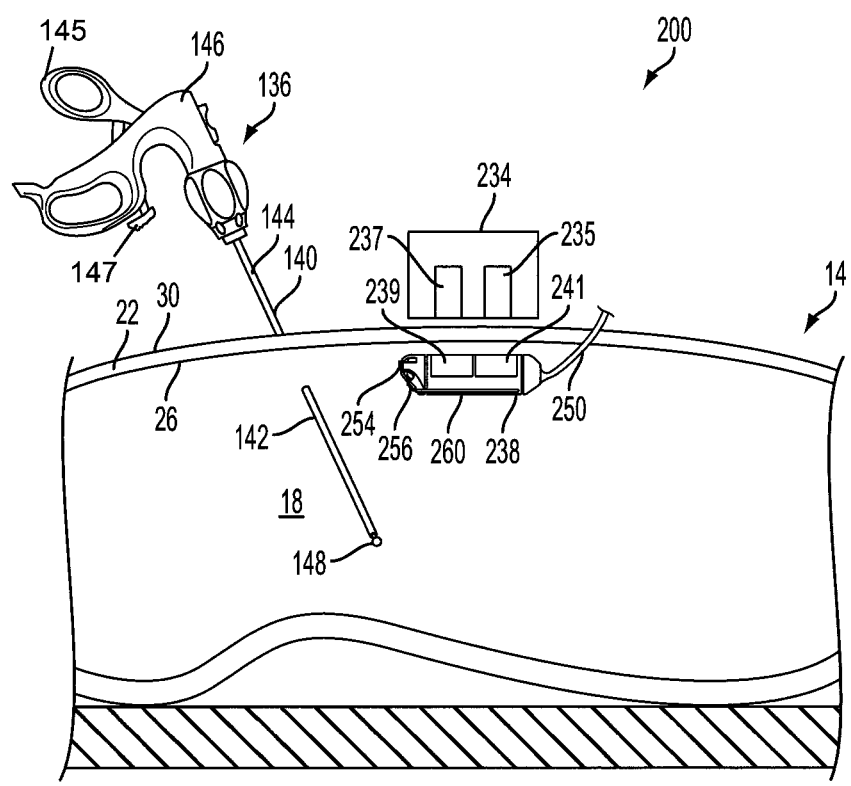
FIG. 7 is schematic view of a patient's body cavity and a surgical system in accordance with at least one embodiment.

Referring Primarily to FIGS. 6A and 7, the in-vivo instrument 238 is substantially similar in many respects to the in-vivo instrument 138. The in-vivo instrument 238 can be introduced into the cavity 18 via an introducer 270, as illustrated in FIG. 6. Several types of introducers that may be utilized, for example, are described in U.S. application Ser. No. 13/325,791, entitled INTRODUCER FOR AN INTERNAL MAGNETIC CAMERA, filed Dec. 14, 2011, the entire disclosure of which is incorporated herein by reference. Furthermore, the in-vivo instrument 238 is positionable (can be positioned), and is shown positioned, within the cavity 18 and near, adjacent to, and/or in contact with the interior surface of wall 22, as illustrated in FIG. 7.

Referring again to FIG. 6A, the in-vivo instrument 238 may be magnetically couplable to the ex-vivo positioning mechanism 234. For example, ex-vivo positioning mechanism 234 can comprise one or more magnets (e.g., permanent magnets, electromagnets, or the like) and in-vivo instrument 238 can comprise a ferromagnetic material. Alternatively, ex-vivo positioning mechanism 234 can comprise one or more magnets, and in-vivo instrument 238 can comprise a ferromagnetic material, such that ex-vivo positioning mechanism 234 attracts in-vivo instrument 238 and in-vivo instrument 238 is attracted to ex-vivo positioning mechanism 234. In yet another example, both ex-vivo positioning mechanism 234 and in-vivo instrument 238 can comprise one or more magnets such that ex-vivo positioning mechanism 234 and in-vivo instrument 238 attract each other. In the example illustrated in FIG. 7, the ex-vivo positioning mechanism comprises magnets 235 and 237, and the in-vivo instrument 238 comprises magnets 239 and 241 which are attracted to magnets 235 and 237, respectively.

Further to the above, the ex-vivo positioning mechanism 234, the in-vivo instrument 238, or both may comprise a sensing mechanism to measure the magnitude of the magnetic force that the ex-vivo positioning mechanism 234 exerts on in-vivo instrument 238 or vice versa. Ex-vivo positioning mechanism 234, in-vivo instrument 238, or both may be further configured to modulate the strength of the magnetic field therebetween as described in U.S. patent application Ser. No. 12/783,449 filed on May 19, 2010, now U.S. Patent Publication No. US 2011/0285488, entitled MAGNETIC THROTTLING AND CONTROL: MAGNETIC CONTROL, the entire disclosure of which is incorporated herein by reference.

Figure 8:
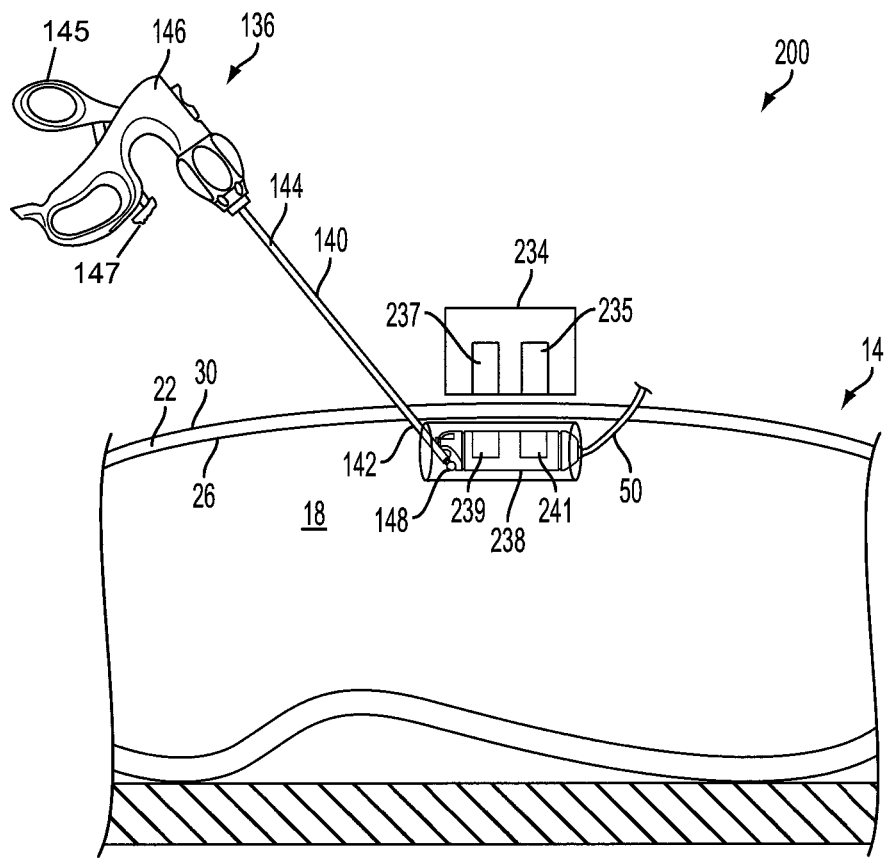
FIG. 8 is schematic view of a patient's body cavity and a surgical system in accordance with at least one embodiment.

Referring primarily to FIGS. 6-7, an operator of the surgical system 200 may introduce the in-vivo instrument 238 into the cavity 18 through an access port in the wall 22, for example, by using the introducer 270. The operator may then magnetically engage the ex-vivo positioning system 234 with the in-vivo instrument 238 through the wall 22, as illustrated in FIG. 8. In addition, the operator may use the ex-vivo positioning mechanism 234 to navigate the in-vivo instrument 234 within cavity 18, for example, to view surrounding tissue via the camera 54 and/or camera 56.

Figure 9:
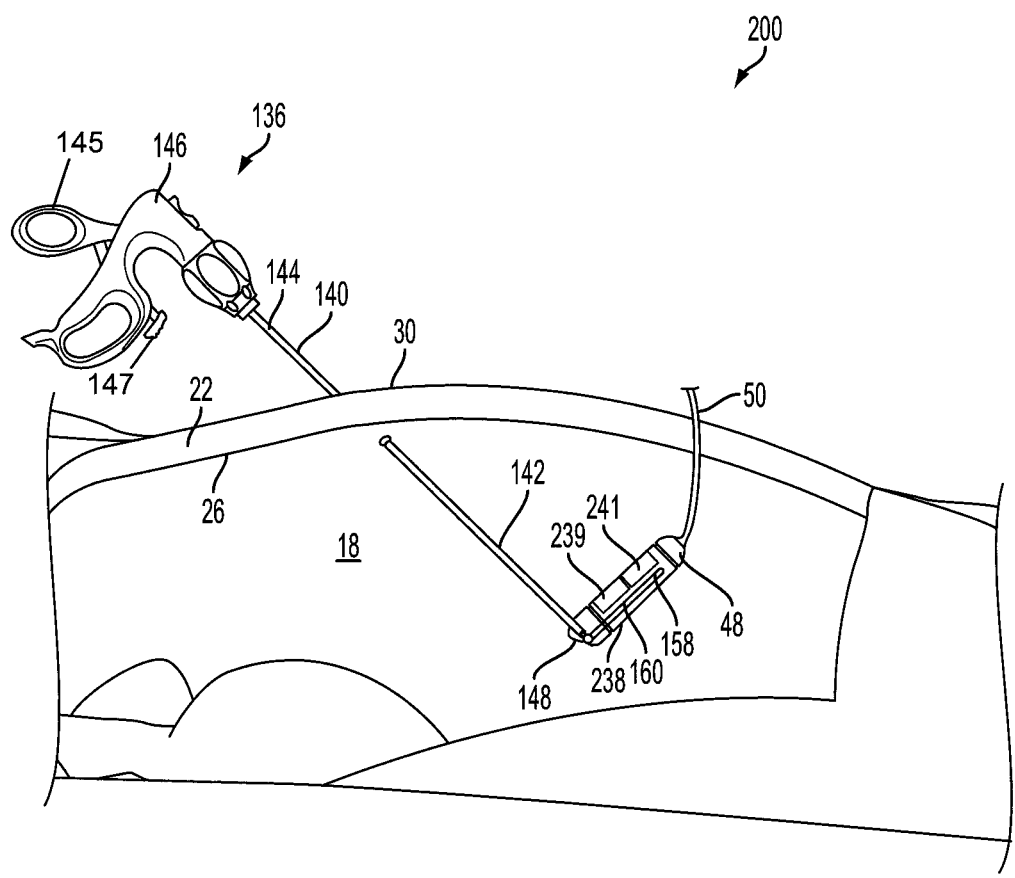
FIG. 9 is schematic view of a patient's body cavity and a surgical system in accordance with at least one embodiment.

Referring now to FIGS. 8 and 9, during the surgical procedure, the operator may choose to navigate another instrument using the ex-vivo positioning mechanism 234. In such a case, the operator may choose to separate the in-vivo instrument 238 from its magnetic coupling to the ex-vivo positioning mechanism 234 and to couple the in-vivo instrument 238 to the percutaneous member 136 in order to free the ex-vivo positioning mechanism 234 for the other instrument. The operator may navigate the ex-vivo positioning mechanism 234 to view another portion of wall 22 via the camera 54, for example, and pierce through that portion of the wall 22 using the needle of the percutaneous member 136. Furthermore, the operator may extend the distal portion 142 of the elongate body 140 into the cavity 18 in view of camera 54, for example. To separate the in-vivo instrument 238 from magnetic coupling with the ex-vivo positioning mechanism 234, the operator may couple the in-vivo instrument 238 to connector 148, as described above, and move the in-vivo instrument 234 in a direction away from the ex-vivo positioning mechanism 234 in order to overcome the attractive forces therebetween. In addition, the operator may selectively lock the connector 148 to the in-vivo instrument 238 by, for example, retracting the elongate shaft 152 relative to the hollow tubular member 150 until the in-vivo instrument 138 is abutted against the distal end of the hollow tubular member 150. The ex-vivo positioning mechanism can then be removed, as illustrated in FIG. 9, or magnetically coupled to the other instrument.

The reader will appreciate that the in-vivo instrument 238 can be toggled within the cavity 18 between being coupled to the ex-vivo positioning mechanism 234 and being coupled to the percutaneous member 138. For example, the in-vivo instrument 238 can be re-coupled to the ex-vivo positioning mechanism 234 by, for example, moving the in-vivo instrument 238 sufficiently close to re-established magnetic coupling with the ex-vivo positioning mechanism 234. The connector 148 can then be released from its locked position, for example, by advancing the elongate shaft 154 relative to the hollow tubular member 152. The enlarged portion 156 can then be retracted from the track 160 through the opening 162 thereby releasing the in-vivo instrument 238 from the coupling engagement with the percutaneous member 136.

The toggling of the in-vivo instrument 238 between the ex-vivo positioning mechanism 234 and the percutaneous member 138 may give the surgical operator freedom to view the surgical site from different angles. For example, a surgical operator performing a surgical procedure such as, for example, removing a gall bladder may elect to transition the in-vivo instrument 238 from the ex-vivo positioning mechanism 234 to the percutaneous member 236 to introduce, for example, grasper into the surgical site via the ex-vivo positioning mechanism.

The reader will appreciate that the in-vivo instrument 238 may include surgical end effectors other than or in addition to a camera. For example, in-vivo surgical instrument 238 may include a grasper, a harmonic blade, and/or a surgical stapler. Other surgical end effectors are also contemplated within the scope of the present disclosure.

A surgical device comprises a percutaneous member which comprises an elongate body including a first distal end portion configured for insertion into a body cavity and a connector at the distal end portion of the elongate body, wherein the connector is selectively movable relative to the distal end portion between locked and unlocked orientations. In addition, the surgical device comprises an in-vivo instrument configured for use within the body cavity, wherein the in-vivo instrument defines a longitudinal axis, wherein the connector is selectively coupled to the in-vivo instrument, and wherein the connector is selectively lockable to the in-vivo instrument at multiple positions along the longitudinal axis.

A surgical system comprises an ex-vivo positioning mechanism, an in-vivo instrument magnetically attracted to the ex-vivo positioning mechanism, whereby the in-vivo instrument can be positioned within a patient by moving the ex-vivo positioning mechanism, and a percutaneous member introducible into the patient independent from the ex-vivo positioning mechanism, the percutaneous member comprising a connector at a distal portion thereof, wherein the connector is selectively couplable to the in-vivo instrument within the patient.

A surgical method comprises passing a camera into a body cavity through an incision in a first portion of a body wall, the camera comprising a lens and a connection portion, magnetically coupling the camera to an ex-vivo positioning mechanism, positioning the camera in the body cavity by operating the ex-vivo positioning mechanism, operating the camera to visualize the body cavity on an external monitor, directing the camera lens toward a second portion of the body wall, passing a distal portion of a percutaneous member into the body cavity through the second portion of the body wall, guiding a connector at the distal portion of the percutaneous member toward the connection portion of the camera, and coupling the connector with the connection portion of the camera.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

While this invention has been described as having exemplary designs, the present invention may be further modified within the spirit and scope of the disclosure. This application is therefore intended to cover any variations, uses, or adaptations of the invention using its general principles. Further, this application is intended to cover such departures from the present disclosure as come within known or customary practice in the art to which this invention pertains.

What is claimed is:

1. A surgical device, comprising:
   a percutaneous member comprising:
      a hollow tubular member including a distal end;
      an elongate shaft including a distal end portion configured for insertion into a body cavity, wherein at least a portion of the elongate shaft is disposed within the hollow tubular member; and
      a connector positioned on the distal end portion of the elongate shaft, the connector having a first contour, wherein the connector is selectively movable relative to the distal end of the hollow tubular member between locked and unlocked orientations, and wherein the connector is permanently impassible through the distal end of the hollow tubular member; and
   an in-vivo instrument configured for use within the body cavity, wherein the in-vivo instrument defines a longitudinal axis, the in-vivo instrument including a track having a second contour with a shape that compliments the first contour, the track configured to movably receive the connector and couple the connector to the in-vivo instrument, and wherein the connector is selectively lockable to the in-vivo instrument at multiple positions along the longitudinal axis.

2. The surgical device of claim 1, wherein the in-vivo instrument comprises at least one camera, and wherein the in-vivo instrument is configured to movably receive the connector through a portion of the track adjacent to the at least one camera.

3. The surgical device of claim 2, wherein the in-vivo instrument further comprises a cleaning feature for cleaning a lens of the at least one camera.

4. The surgical device of claim 1, wherein the connector comprises a mating member adapted for sliding engagement with the track.

5. The surgical device of claim 1, wherein the elongate shaft operably interfaces with a handle including a locking means for selectively locking the connector in any of the multiple positions along the track.

6. The surgical device of claim 1, wherein the connector is impassible through the distal end of the hollow tubular member when the connector is in the locked orientation and when the connector is in the unlocked orientation.

7. The surgical device of claim 1, wherein the connector is selectively lockable to the in-vivo instrument at multiple pre-determined positions.

8. A surgical device, comprising:
   an in-vivo instrument configured for use within a body cavity, wherein the in-vivo instrument defines a longitudinal axis, the in-vivo instrument including a track having a first contour; and
   a percutaneous member, comprising:
      a tubular member comprising a distal end; and
      an elongate shaft configured to be positioned within the tubular member, wherein the elongate shaft comprises a connector at a distal portion thereof, the connector having a second contour with a shape that compliments the first contour, wherein the connector is selectively movable relative to the distal end of the tubular member between locked and unlocked orientations, wherein the connector is permanently impassible through the distal end of the tubular member, wherein the connector is configured to be selectively coupled to the in-vivo instrument, and wherein the connector is selectively lockable to the in-vivo instrument at multiple positions along the longitudinal axis.

9. The surgical device of claim 8, wherein the in-vivo instrument is introducible into the body cavity independent from the percutaneous member.

10. The surgical device of claim 8, wherein the in-vivo instrument comprises at least one camera, and wherein the in-vivo instrument is configured to movably receive the connector through a portion of the track adjacent to the at least one camera.

11. The surgical device of claim 10, wherein the in-vivo instrument further comprises a cleaning feature for cleaning a lens of the at least one camera.

12. The surgical device of claim 8, wherein the connector comprises a mating member adapted for sliding engagement with the track.

13. The surgical device of claim 8, wherein the elongate shaft operably interfaces with a handle, and wherein the handle comprises a locking means for selectively locking the connector in any of the multiple positions along the track.

14. A surgical device, comprising:
   a percutaneous member, comprising:
      a tubular member comprising a distal end;
      an elongate shaft comprising a distal end portion; and
      a connector positioned at the distal end portion of the elongate shaft, the connector having a first contour, wherein the connector is selectively movable relative to the distal end of the tubular member between locked and unlocked orientations, and wherein the connector is permanently impassible through the distal end of the tubular member; and
   an in-vivo instrument defining a longitudinal axis, the in-vivo instrument including a track having a second contour with a shape that compliments the first contour, wherein the connector is selectively coupled to the in-vivo instrument, and wherein the connector is selectively lockable to the in-vivo instrument at multiple positions along the longitudinal axis.

15. The surgical device of claim 14, wherein the in-vivo instrument comprises at least one camera, and wherein the in-vivo instrument is configured to movably receive the connector therein through a portion of the track adjacent to the at least one camera.

16. The surgical device of claim 15, wherein the in-vivo instrument further comprises a cleaning feature for cleaning a lens of the at least one camera.

* * * * *